United States Patent
Penning et al.

(10) Patent No.: US 8,383,624 B2
(45) Date of Patent: Feb. 26, 2013

(54) PYRROLOPYRAZINE INHIBITORS OF KINASES

(75) Inventors: Thomas D. Penning, Elmhurst, IL (US); Virajkumar B. Gandhi, Gurnee, IL (US); Gui-Dong Zhu, Gurnee, IL (US); Yunsong Tong, Libertyville, IL (US); Keith W. Woods, Libertyville, IL (US); Chunqiu Lai, Libertyville, IL (US); Jane Gong, Deerfield, IL (US); Alan S. Florjancic, Kenosha, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/836,637

(22) Filed: Jul. 15, 2010

(65) Prior Publication Data

US 2011/0015172 A1 Jan. 20, 2011

Related U.S. Application Data

(60) Provisional application No. 61/225,770, filed on Jul. 15, 2009.

(51) Int. Cl.
*A61K 31/495* (2006.01)
(52) U.S. Cl. ........ 514/249; 544/333; 544/350; 546/210; 546/268.1; 548/518; 549/505
(58) Field of Classification Search .................. 514/249; 544/333, 350; 546/210, 268.1; 548/518; 549/505
See application file for complete search history.

(56) References Cited

U.S. PATENT DOCUMENTS

2006/0258662 A1* 11/2006 Binch et al. .................. 514/249
2007/0043063 A1 2/2007 Salituro et al.
2007/0293491 A1 12/2007 Shafer et al.

FOREIGN PATENT DOCUMENTS

| CA | 2648809 A1 | 11/2007 |
|---|---|---|
| WO | WO9822457 A1 | 5/1998 |
| WO | WO2004078756 A2 | 9/2004 |
| WO | WO2005095400 A1 | 10/2005 |
| WO | WO2006058074 A1 | 6/2006 |
| WO | WO2007107221 A1 | 9/2007 |

OTHER PUBLICATIONS

Cho, W.H. et al., "CDC7 kinase phosphorylates serine residues adjacent to acidic amino acids in the minichromosome maintenance 2 protein," Proceedings of the National Academy of Sciences, 2006, vol. 103 (31), pp. 11521-11526.

Feng, D. et al., "Inhibiting the expression of DNA replication-initiation proteins induces apoptosis in human cancer cells," Cancer Res., 2003, pp. 7356-7364, vol. 63.
Guo, B. et al., "High Levels of Cdc7 and Dbf4 Proteins Can Arrest Cell-Cycle Progression," European Journal of Cell Biology, 2005, vol. 84, pp. 927-938.
International Search Report and Written Opinion for Application No. PCT/US2010/041935 mailed on Sep. 15, 2010, 9 pages.
Kim, J. M. et al., "Functions of mammalian Cdc7 kinase in initiation/monitoring of DNA replication and development," Mutat. Res., 2003, pp. 29-40, vol. 532 (1-2).
Kim, J. M. et al., "Genetic dissection of mammalian Cdc7 kinase: cell cycle and developmental roles," Cell Cycle, 2004, pp. 300-304, vol. 3 (3).
Kim, J.M. et al., "Inactivation of Cdc7 Kinase in Mouse ES Cells Results in S-Phase Arrest and p53-Dependent Cell Death," The EMBO Journal, 2002, vol. 21 (9), pp. 2168-2179.
Lau, E. et al., "Is there a pre-RC checkpoint that cancer cells lack?," Cell Cycle, 2006, pp. 1602-1606, vol. 5 (15).
Lau, E. et al., "The functional role of Cdc6 in S-G2/M in mammalian cells," EMBO Rep., 2006, pp. 425-430, vol. 7.
Lau, E. et al., "The role of pre-replicative complex (pre-RC) components in oncogenesis," Faseb J., 2007, pp. 3786-3794, vol. 21 (14).
Montagnoli, A. et al., "Cdc7 inhibition reveals a p53- dependent replication checkpoint that is defective in cancer cells," Cancer Res., 2004, pp. 7110-7116, vol. 64.
Montagnoli, A. et al., "Identification of Mcm2 phosphorylation sites by S-phase-regulating kinases," The Journal of Biological Chemistry, 2006, vol. 281 (15), pp. 10281-10290.
Stillman, B., "Origin recognition and the chromosome cycle," FEBS Lett., 2005, pp. 877-884, vol. 579.
Tsuji, T. et al., "Essential Role of Phosphorylation of MCM2 by Cdc7/Dbf4 in the Initiation of DNA Replication in Mammalian Cells," Molecular Biology of the Cell, 2006, vol. 17, pp. 4459-4472.

* cited by examiner

Primary Examiner — Douglas M Willis
(74) Attorney, Agent, or Firm — Susan L. Steele

(57) ABSTRACT

The present invention relates to compounds of formula (I) or pharmaceutical acceptable salts,

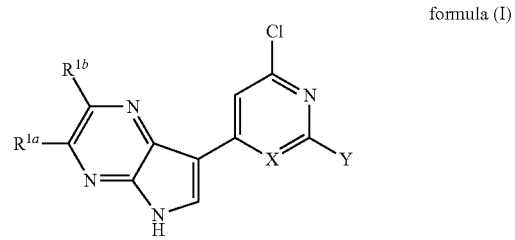

formula (I)

wherein $R^{1a}$, $R^{1b}$, X, and Y are defined in the description. The present invention relates also to compositions containing said compounds which are useful for inhibiting kinases such as Cdc7 and methods of treating diseases such as cancer.

11 Claims, No Drawings

PYRROLOPYRAZINE INHIBITORS OF KINASES

CROSS-REFERENCE TO RELATED APPLICATIONS

This application claims priority to U.S. Provisional Application Ser. No. 61/225,770 filed Jul. 15, 2009, which is incorporated by reference in its entirety.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATED-BY-REFERENCE OF MATERIAL SUBMITTED ON A COMPACT DISC

Not Applicable.

BACKGROUND OF THE INVENTION

Eukaryotic cells divide by a directed, step-wise process referred to as the cell cycle. Cells must first replicate their DNA in S phase before separating their sister chromatids in mitosis (karyokinesis) and splitting off into two daughter cells (cytokinesis). In mammalian cells, DNA replication must be initiated at multiple sites (replication origins) throughout the genome to ensure that all the genetic material is duplicated prior to mitosis. To maintain genome integrity, DNA must be replicated only once per cell cycle, and so this process is highly regulated and governed by checkpoints. Before replication is initiated, origins must be licensed through the formation of pre-replication complexes (pre-RCs) in early G1. Formation of pre-RCs involves the step-wise binding of the origin recognition complex (ORC) to origins followed by the binding of the loading factors Cdc6 and Cdt1. These proteins then recruit the putative DNA replicative helicase complex, MCM2-7. Once this pre-RC is formed, replication initiation requires the activation of S-phase-promoting serine/threonine kinases, Cyclin/Cdks and Cdc7/Dbf4. These kinases consist of an enzymatic sub-unit (CDKs and Cdc7) and a regulatory sub-unit (Cyclins for CDKs; Dbf4 or Drf1 for Cdc7). They phosphorylate multiple MCMs in pre-RCs in a sequential manner, thereby activating the helicase and recruiting other DNA replication factors (Cdc45, GINS complex, etc.) for DNA synthesis (for reviews, see Kim et al., 2003; Kim et al., 2004; Lau et al., 2006; Lau et al., 2007; Stillman, 2005). MCM2 Serine-40 and Serine-53 are well-characterized phosphorylation sites for Cdc7/Dbf4 (Cho et al., 2006; Montagnoli et al., 2006; Tsuji et al., 2006).

Inhibiting regulators of replication initiation, such as Cdc6, Cdc7/Dbf4 or Cdc7/Drf1, has lethal consequences in cancerous cells, whereas normal cells are able to arrest and resume normal divisions once initiation activity is restored (Feng et al., 2003; Montagnoli et al., 2004; see Lau and Jiang, 2006, for review). Small molecule inhibitors of the protein kinase Cdc7 are thus attractive candidates for therapeutic intervention in cancer, inflammation and other cell proliferative disorders.

BRIEF SUMMARY OF THE INVENTION

The present invention has numerous embodiments. One embodiment of this invention, therefore, pertains to compounds that have formula (I)

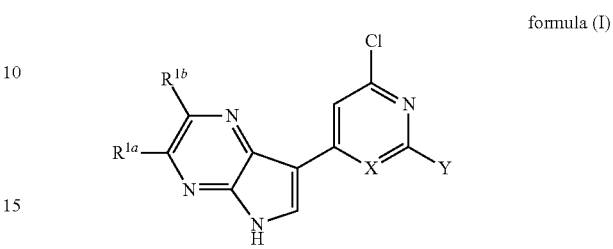

formula (I)

wherein $R^{1a}$, and $R^{1b}$, X, and Y are as defined below and subsets therein.

Also provided are pharmaceutically acceptable compositions comprising a therapeutically effective amount of a compound of formula (I) a pharmaceutically acceptable salt in combination with a pharmaceutically suitable carrier.

One embodiment is directed a method of treating cancer in a mammal comprising administering thereto a therapeutically acceptable amount of a compound or pharmaceutically acceptable salt of formula (I). In yet another embodiment pertains to a method of decreasing tumor volume in a mammal comprising administering thereto a therapeutically acceptable amount of a compound or pharmaceutically acceptable salt of formula (I).

BRIEF DESCRIPTION OF THE SEVERAL VIEWS OF THE DRAWING(S)

Not Applicable.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

ABBREVIATIONS AND DEFINITIONS

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight-or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1] hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-N-pyridinyl, pyrido[3,2-b]-N-pyridinyl, or pyrido[4,3-b]-N-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$- prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase.

Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

In one aspect, the present invention provides compounds of formula (I):

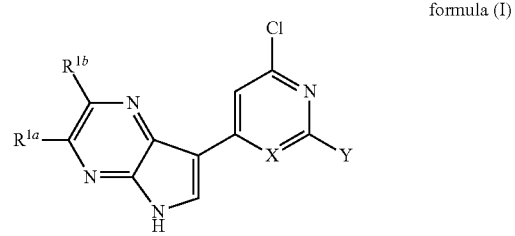

formula (I)

wherein $R^{1a}$ and $R^{1b}$ are independently hydrogen, hydroxy, nitro, halogen, cyano, trifluoromethyl, trifluoromethoxy, $C_{1-4}$-alkyl, $C_{1-4}$-alkenyl, aryl, heteroaryl, —OR$^a$, —NR$^b$R$^c$; —C(O)OR$^a$, —C(O)NR$^b$R$^c$, —NR$^b$C(O)R$^c$, —NHC(O)NHR$^b$, or —NHSO$_2$R$^a$, wherein the $C_{1-4}$-alkenyl can be optionally substituted with and wherein the aryl or heteroaryl can be optionally substituted with one or more R$^k$;

X is N or CR$^2$;

$R^2$ is hydrogen or $C_{1-4}$-alkyl;

Y is NR$^3$R$^4$, NR$^6$C(O)R$^7$, NR$^6$SO$_2$R$^7$, aryl, or heteroaryl, wherein the aryl and heteroaryl are optionally substituted with one or more R$^5$;

$R^3$ is hydrogen, $C_{1-8}$-alkyl, $C_{2-8}$-alkenyl, $C_{2-8}$-alkynyl, $C_{3-8}$-cycloalkyl, $C_{3-8}$-cycloalkyl-($C_{1-8}$-alkyl)-, heterocycloalkyl, heterocycloalkyl-($C_{1-8}$-alkyl)-, aryl, aryl-($C_{1-8}$-alkyl)-, heteroaryl-, or heteroaryl-($C_{1-8}$-alkyl)-, wherein (a) the R$^3$C$_{1-8}$-alkyl, C$_{2-8}$-alkenyl, C$_{2-8}$-alkynyl substituents, alone or as part of another group, are optionally substituted with one or more substituents selected from the group consisting of halogen, cyano, nitro, oxo, —OR$^a$, —C(O)R$^a$, —C(O)OR$^a$, —OC(O)R$^a$, —NR$^b$R$^c$, —NR$^b$C(O)R$^a$, —NHC(O)NHR$^b$, —C(O)NR$^b$R$^c$, —NHSO$_2$R$^a$, —SO$_2$NR$^b$NR$^c$, and benzyl; and (b) the R$^3$C$_{3-8}$-cycloalkyl, heterocycloalkyl, aryl, and heteroaryl, alone or as part of another group, are optionally substituted with one or more R$^5$;

$R^4$ is hydrogen or $C_{1-8}$-alkyl; wherein the $C_{1-8}$-alkyl is optionally substituted with one or more substituents selected from the group consisting of halogen, cyano, oxo, —OR$^a$, —C(O)R$^a$, —C(O)OR$^a$, —OC(O)R$^a$, —NR$^b$R$^c$, —NR$^b$C(O)R$^a$, —NHC(O)NHR$^b$, —C(O)NR$^b$R$^c$, —NHSO$_2$R$^a$, and —SO$_2$NR$^b$NR$^c$;

or $R^3$ and $R^4$ can be joined together to form a 4-7 membered heterocycloalkyl ring; wherein the heterocycloalkyl ring is optionally substituted with one or more $R^5$;

$R^5$ is selected from the group consisting of $C_{1-8}$-alkyl, $C_{2-8}$-alkenyl, $C_{2-8}$-alkynyl, aryl, heterocyclyl, halogen, oxo, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$NHSO_2R^d$, —$C(O)NR^eR^f$, —$SR^d$, —$S(O)R^d$, —$SO_2R^d$, —$SO_2NR^eNR^f$, —$B(OH)_2$, —$CF_3$, —$CF_2CF_3$, —$OCF_3$, and —$OCF_2CF_3$ wherein (a) the $R^5 C_{1-8}$-alkyl, $C_{2-8}$-alkenyl, $C_{2-8}$-alkynyl, substituents are optionally substituted with one or more substituents selected from the group consisting of aryl, heterocyclyl, $C_{3-8}$-cycloalkyl, halogen, cyano, nitro, oxo, —$OR^d$, —$C(O)R^d$, —$C(O)OR^d$, —$OC(O)R^d$, —$NR^eR^f$, —$NR^eC(O)R^d$, —$NHC(O)NHR^e$, —$C(O)NR^eR^f$; and wherein (b) the $R^5$ aryl or heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, oxo —$OR^g$, —$C(O)R^g$, —$C(O)OR^g$, —$OC(O)R^g$, —$NR^hR^i$, —$NR^hC(O)R^g$, —$NHC(O)NHR^h$, —$NHSO_2R^g$, —$C(O)NR^hR^i$, —$SR^g$, —$S(O)R^g$, —$SO_2R^g$, —$SO_2NR^hNR^i$, —$CF_3$, —$CF_2CF_3$, —$OCF_3$, and —$OCF_2CF_3$;

$R^6$ is hydrogen or $C_{1-8}$-alkyl;

$R^7$ is hydrogen, $C_{1-8}$-alkyl, $C_{2-8}$-alkenyl, $C_{2-8}$-alkynyl, $C_{3-8}$-cycloalkyl, $C_{3-8}$-cycloalkyl-($C_{1-8}$-alkyl)-, heterocycloalkyl, heterocycloalkyl-($C_{1-8}$-alkyl)-, aryl, aryl-($C_{1-8}$-alkyl)-, heteroaryl-, or heteroaryl-($C_{1-8}$-alkyl)-, wherein (a) the $R^7 C_{1-8}$-alkyl, $C_{2-8}$-alkenyl, $C_{2-8}$-alkynyl substituents, alone or as part of another group, are optionally substituted with one or more substituents selected from the group consisting of halogen, cyano, nitro, oxo, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, —$SO_2NR^bR^c$, and benzyl; and (b) the $R^7 C_{3-8}$-cycloalkyl, heterocycloalkyl, aryl, and heteroaryl, alone or as part of another group, are optionally substituted with one or more $R^5$;

$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl$)_2$;

$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^b$ and $R^c$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl$)_2$;

$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl$)_2$;

$R^e$ and $R^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^e$ and $R^f$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl$)_2$;

$R^g$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl$)_2$;

$R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^i$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl$)_2$;

$R^j$ is selected from the group consisting of aryl, heterocyclyl, and $C_{3-8}$-cycloalkyl wherein aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl$)_2$, and $R^k$, at each occurrence, is independently selected from the group consisting of hydroxy, $C_{1-8}$-alkoxy, CN, halogen, $C_{1-8}$-alkyl, heterocyclyl, and $C_{3-8}$-cycloalkyl, wherein the $C_{1-8}$-alkyl, heterocyclyl, and $C_{3-8}$-cycloalkyl, are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl$)_2$; or a pharmaceutically acceptable salt thereof.

In one embodiment of formula (I), $R^{1a}$ and $R^{1b}$ are each hydrogen. In another embodiment, $R^{1b}$ is hydrogen and $R^{1a}$ is hydroxy, nitro, halogen, cyano, trifluoromethyl, trifluoromethoxy, $C_{1-4}$-alkyl, —$OR^a$, —$NR^bR^c$, —$C(O)OR^a$, —$C(O)NR^bR^c$, —$NR^bC(O)R^c$, —$NHC(O)NHR^b$, or —$NHSO_2R^a$. In another embodiment, $R^{1a}$ is hydrogen and $R^{1b}$ is hydroxy, nitro, halogen, cyano, trifluoromethyl, trifluoromethoxy, $C_{1-4}$-alkyl, —$OR^a$, —$NR^bR^c$, —$C(O)OR^a$, —$C(O)NR^bR^c$, —$NR^bC(O)R^c$, —$NHC(O)NHR^b$, or —$NHSO_2R^a$.

In one embodiment of formula (I), X is N.

In another embodiment of formula (I), X is $CR^2$ wherein $R^2$ is hydrogen or methyl. In yet another embodiment, $R^2$ is hydrogen.

In one embodiment of formula (I), Y is aryl or heteroaryl. In another embodiment, the aryl or heteroaryl groups are unsubstituted. In yet another embodiment, aryl or heteroaryl groups are substituted with one, two, or three $R^5$.

In yet another embodiment of formula (I), Y is a heteroaryl group selected from the group consisting of furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, and pyrazinyl.

In another embodiment of formula (I), Y is a phenyl group. Preferably, where Y is a substituted phenyl, the phenyl is substituted with one, two, or three substituents independently selected from the group consisting of fluoro, chloro, methyl, ethyl, methoxy, ethoxy, —$CF_3$, —$CF_2CF_3$, —$OCF_3$, —$OCF_2CF_3$, and cyano.

In one preferred embodiment of formula (I), Y is $NR^3R^4$.

In one embodiment of formula (I), $R^3$ is optionally substituted $C_{1-8}$-alkyl or optionally substituted $C_{2-8}$-alkenyl. In one embodiment, the $R^3C_{1-8}$-alkyl or $C_{2-8}$-alkenyl is unsubstituted. In another embodiment, the $R^3C_{1-8}$-alkyl or $C_{2-8}$-alkenyl is substituted with one or two substituents as defined above. Preferably, the one or two substituents are independently selected from the groups consisting of oxo, —$OR^a$— $NR^bR^c$, —$NR^bC(O)R^a$, —$NHSO_2R^a$, —$SO_2NR^bNR^c$, and benzyl, wherein $R^a$, $R^b$, and $R^c$ are independently selected from the group consisting of H and $C_{1-8}$-alkyl. More preferably, the $R^3C_{1-8}$-alkyl or $C_{2-8}$-alkenyl is optionally substituted with one or two substituents selected from the group consisting of hydroxy, methoxy, ethoxy, amino, —$NHCH_3$, —$NHCOCH_3$, —$NHSO_2CH_3$, and —$SO_2NHCH_3$.

Where $R^3$ is optionally substituted $C_{1-8}$-alkyl, then preferably $R^3$ is methyl, ethyl, propyl, isopropyl, n-butyl, sec-butyl, t-butyl, 3-methylbutan-1-yl, pentyl, neopentyl, or 4,4-dimethylpentan-1-yl.

Where $R^3$ is optionally substituted $C_{2-8}$-alkenyl, then preferably $R^3$ is vinyl, prop-2-enyl, or but-3-enyl.

In another embodiment of formula (I), $R^3$ is aryl or heteroaryl. In one embodiment of formula (I), $R^3$ is phenyl optionally substituted with one or more $R^5$. In another embodiment of formula (I), $R^3$ is a 5-7-membered heteroaryl optionally substituted with one or more $R^5$. In yet another embodiment, $R^3$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, and more preferably pyridinyl.

In one embodiment of formula (I), $R^3$ is an optionally substituted $C_{3-8}$-cycloalkyl or an optionally substituted heterocycloalkyl. In one embodiment, the $R^3C_{3-8}$-cycloalkyl or heterocycloalkyl is unsubstituted. In another embodiment, the $R^3C_{3-8}$-cycloalkyl or heterocycloalkyl is substituted with one or two $R^5$. Preferably, the one or two substituents are independently selected from the groups consisting of $C_{1-8}$-alkyl, halogen, —$OR^d$, —$NR^eR^f$, $NR^eC(O)R^d$, —$NHSO_2R^d$, and —$SO_2NR^eNR^f$, wherein $R^d$, $R^e$, and $R^f$ are independently selected from the group consisting of H, $C_{1-8}$-alkyl, $C_{3-8}$-cycloalkyl, 4-7-membered heterocycloalkyl, phenyl, and pyridinyl. More preferably, the $R^3C_{3-8}$-cycloalkyl or heterocycloalkyl is optionally substituted with one or two substituents selected from the group consisting of hydroxy, methoxy, ethoxy, amino, —$NHCH_3$, —$NHCOCH_3$, —$NHSO_2CH_3$, and —$SO_2NHCH_3$.

Where $R^3$ is optionally substituted $C_{3-8}$-cycloalkyl, then preferably $R^3$ is cyclobutyl, cyclopentyl, or cyclohexyl. More preferably, $R^3$ is cyclohexyl.

Where $R^3$ is optionally substituted heterocycloalkyl, then preferably $R^3$ is an optionally substituted 5-7 membered heterocycloalkyl. In another embodiment, the $R^3$ heterocycicoalkyl is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, and 2,6-dioxopiperidinyl. Preferably, $R^3$ is pyrrolidinyl, tetrhydrofuryl, piperidinyl, or tetrahydropyranyl.

In another embodiment of formula (I), $R^3$ is $C_{3-8}$-cycloalkyl-($C_{1-8}$-alkyl), heterocycloalkyl-($C_{1-8}$-alkyl), aryl-($C_{1-8}$-alkyl)-, or heteroaryl-($C_{1-8}$-alkyl), wherein (a) the $R^3$—($C_{1-8}$-alkyl)- is optionally substituted with one or more substituents selected from the group consisting of halogen, cyano, nitro, oxo, —$OR^a$, —$C(O)R^a$, —$C(O)OR^a$, —$OC(O)R^a$, —$NR^bR^c$, —$NR^bC(O)R^a$, $NHC(O)NHR^b$, —$C(O)NR^bR^c$, —$NHSO_2R^a$, —$SO_2NR^bNR^c$, and benzyl; and (b) the $R^3C_{3-8}$-cycloalkyl, heterocycloalkyl, aryl, and heteroaryl are optionally substituted with one or more $R^5$.

In one embodiment, where $R^3$ is $C_{3-8}$-cycloalkyl-($C_{1-8}$-alkyl)-, heterocycloalkyl-($C_{1-8}$-alkyl)-, aryl-($C_{1-8}$-alkyl)-, or heteroaryl-($C_{1-8}$-alkyl)-, the $R^3$—($C_{1-8}$-alkyl)- is unsubstituted.

In one embodiment, where $R^3$ is $C_{3-8}$-cycloalkyl-($C_{1-8}$-alkyl)-, heterocycloalkyl-($C_{1-8}$-alkyl)-, aryl-($C_{1-8}$-alkyl)-, or heteroaryl-($C_{1-8}$-alkyl), the $R^3$ cycloalkyl, heterocycloalkyl, aryl, or heteroaryl is unsubstituted. In another embodiment, the $R^3$ cycloalkyl, heterocycloalkyl, aryl, or heteroaryl is optionally substituted with one or two $R^5$, wherein the one or two substituents are independently selected from the groups consisting of $C_{1-8}$-alkyl, halogen, —$OR^d$, —$NR^eR^f$, —$NR^eC(O)R^d$, —$NHSO_2R^d$, and —$SO_2NR^eNR^f$, wherein $R^d$, $R^e$, and $R^f$ are independently selected from the group consisting of H, $C_{1-8}$-alkyl, $C_{3-8}$-cycloalkyl, 4-7-membered heterocycloalkyl, phenyl, and pyridinyl. More preferably, the $R^3C_{3-8}$-cycloalkyl or heterocycloalkyl is optionally substituted with one or two substituents selected from the group consisting of hydroxy, methoxy, ethoxy, amino, —$NHCH_3$, —$NHCOCH_3$, —$NHSO_2CH_3$, and —$SO_2NHCH_3$.

Preferably, where $R^3$ is $C_{3-8}$-cycloalkyl-($C_{1-8}$-alkyl), heterocycloalkyl-($C_{1-8}$-alkyl)-, aryl-($C_{1-8}$-alkyl), or heteroaryl-($C_{1-8}$-alkyl), the —($C_{1-8}$-alkyl)- is —($C_1$-alkyl)-, —($C_2$-alkyl)-, or —($C_3$-alkyl)-, and more preferably —($C_1$-alkyl)-.

In one embodiment, where $R^3$ is $C_{3-8}$-cycloalkyl-($C_{1-8}$-alkyl)-, the $C_{3-8}$-cycloalkyl is optionally substituted cyclobutyl, cyclopentyl, or cyclohexyl.

In one embodiment, where $R^3$ is heterocycloalkyl-($C_{1-8}$-alkyl), the heterocycloalkyl is an optionally substituted 5-7 membered heterocycloalkyl. In another embodiment, the $R^3$ heterocycicoalkyl is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, and preferably pyrrolidinyl, tetrhydrofuryl, piperidinyl, or tetrahydropyranyl.

In one embodiment, where $R^3$ is aryl-($C_{1-8}$-alkyl), the aryl is an optionally substituted phenyl.

In one embodiment, where $R^3$ is heteroarylaryl-($C_{1-8}$-alkyl), the heteroaryl is an optionally substituted 5-7-membered heteroaryl. In yet another embodiment, the $R^3$ heteroaryl is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, and more preferably pyridinyl.

In one embodiment of formula (I), $R^4$ is hydrogen. In another embodiment of formula (I), $R^4$ is an unsubstituted branched or straight chain $C_{1-8}$ alkyl. In yet another embodiment of formula (I), $R^4$ is methyl, ethyl, propyl, isopropyl, n-butyl, sec-butyl, or t-butyl. Where $R^4$ is an unsubstituted branched or straight chain $C_{1-8}$ alkyl, then preferably $R^4$ is methyl. In another embodiment of formula (I), $R^4$ is a substituted branched or straight chain $C_{1-8}$ alkyl, wherein the $C_{1-8}$- alkyl is substituted with —OR$^a$ or —NR$^b$R$^c$, wherein R$^a$, R$^b$, and R$^c$ are independently selected from the group consisting of H and C$_{1-8}$-alkyl.

In one embodiment of formula (I), R$^3$ and R$^4$ can be joined together to form a heterocycloalkyl ring, wherein the heterocycloalkyl ring is optionally substituted with one or more R$^5$. In another embodiment, R$^3$ and R$^4$ are joined together to form a 4-7 membered heterocycloalkyl, wherein the heterocycloalkyl is unsubstituted or substituted with one or two R$^5$.

Preferably, the one or two substituents independently selected from the groups consisting of C$_{1-8}$-alkyl, halogen, —OR$^d$, —NR$^e$R$^f$, —NR$^e$C(O)R$^d$, —NHSO$_2$R$^d$, and —SO$_2$NR$^e$NR$^f$, wherein R$^d$, R$^e$, and R$^f$ are independently selected from the group consisting of H, C$_{1-8}$-alkyl, C$_{3-8}$-cycloalkyl, 4-7-membered heterocycloalkyl, phenyl, and pyridinyl. More preferably, the heterocycloalkyl is optionally substituted with one or two substituents selected from the group consisting of hydroxy, methoxy, ethoxy, amino, —NHCH$_3$, —NHCOCH$_3$, —NHSO$_2$CH$_3$, and —SO$_2$NHCH$_3$.

In one embodiment where R$^3$ and R$^4$ are joined together to form a 4-7 membered heterocycloalkyl, the heterocycloalkyl is azetidinyl, pyrrolidinyl, imidazolidinyl, pyrazolidinyl, piperidinyl, piperazinyl, morpholinyl, 2-pyrrolidinyl, 2,5-dioxopyrrolidinyl, 2-oxopiperidinyl, 4-oxopiperidinyl, or 2,6-dioxopiperidinyl, and preferably pyrrolidinyl, tetrhydrofuryl, piperidinyl, or tetrahydropyranyl.

Preferably, NR$^3$R$^4$ is selected from the group consisting of

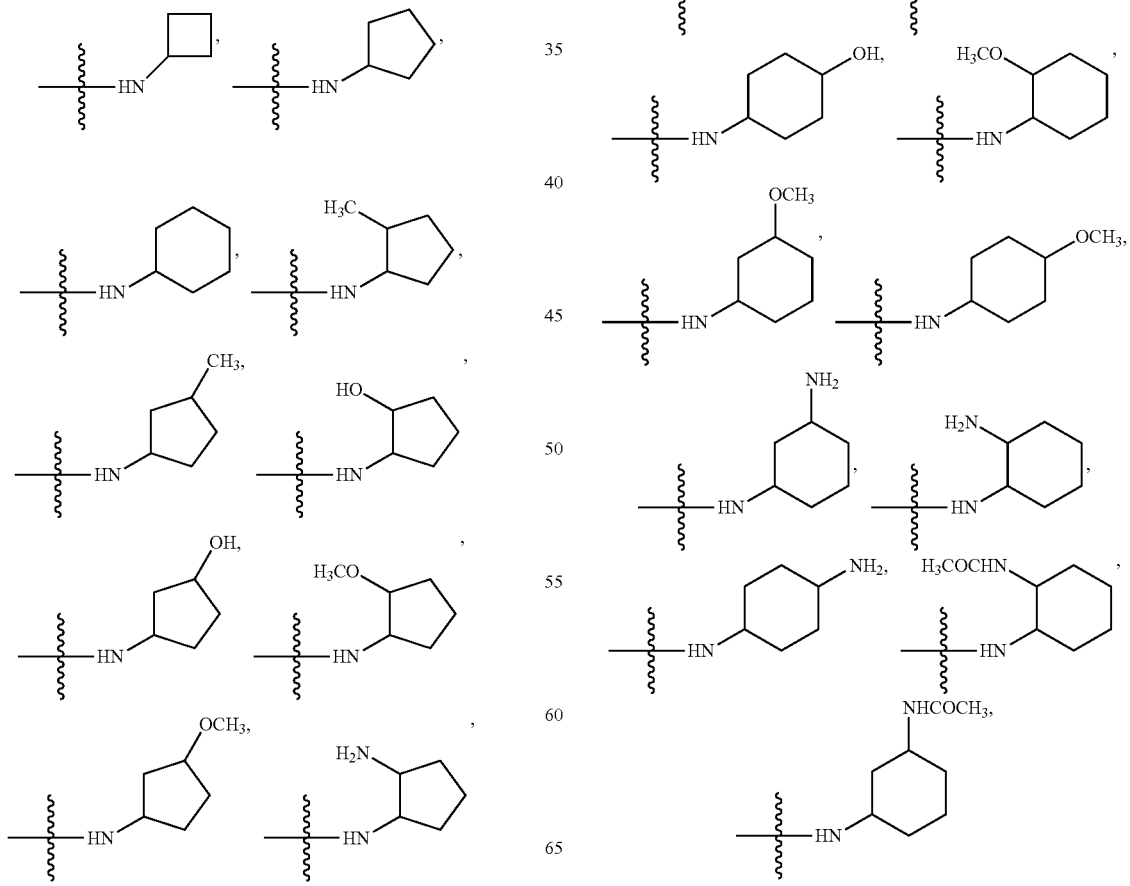

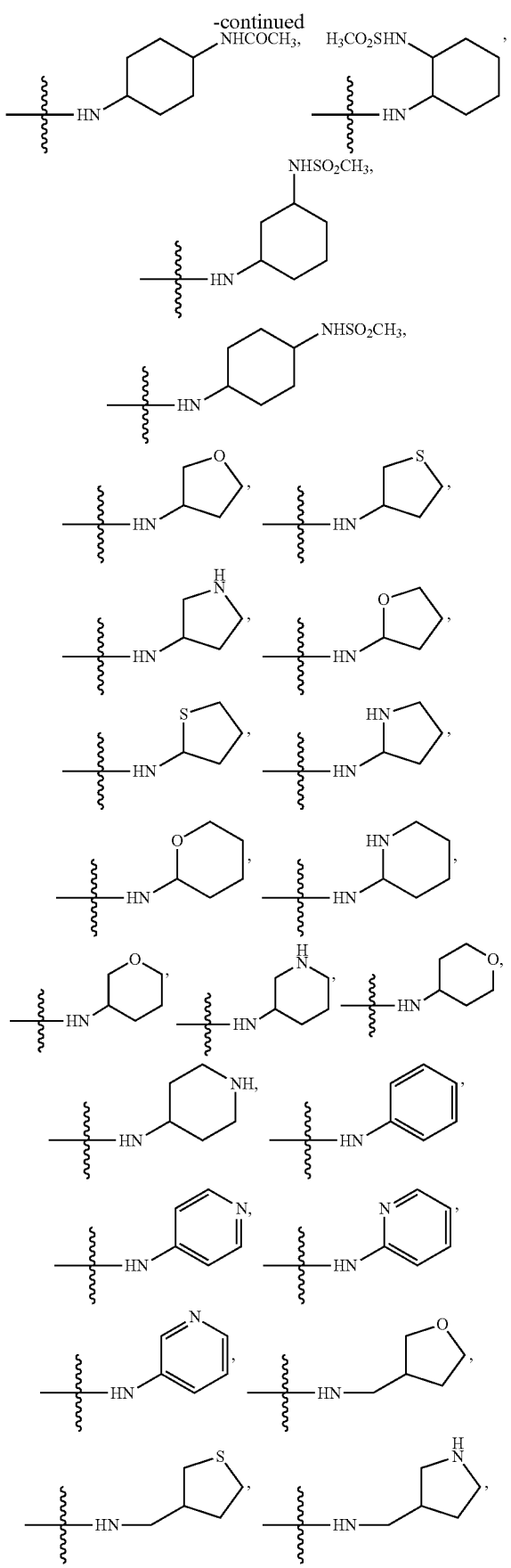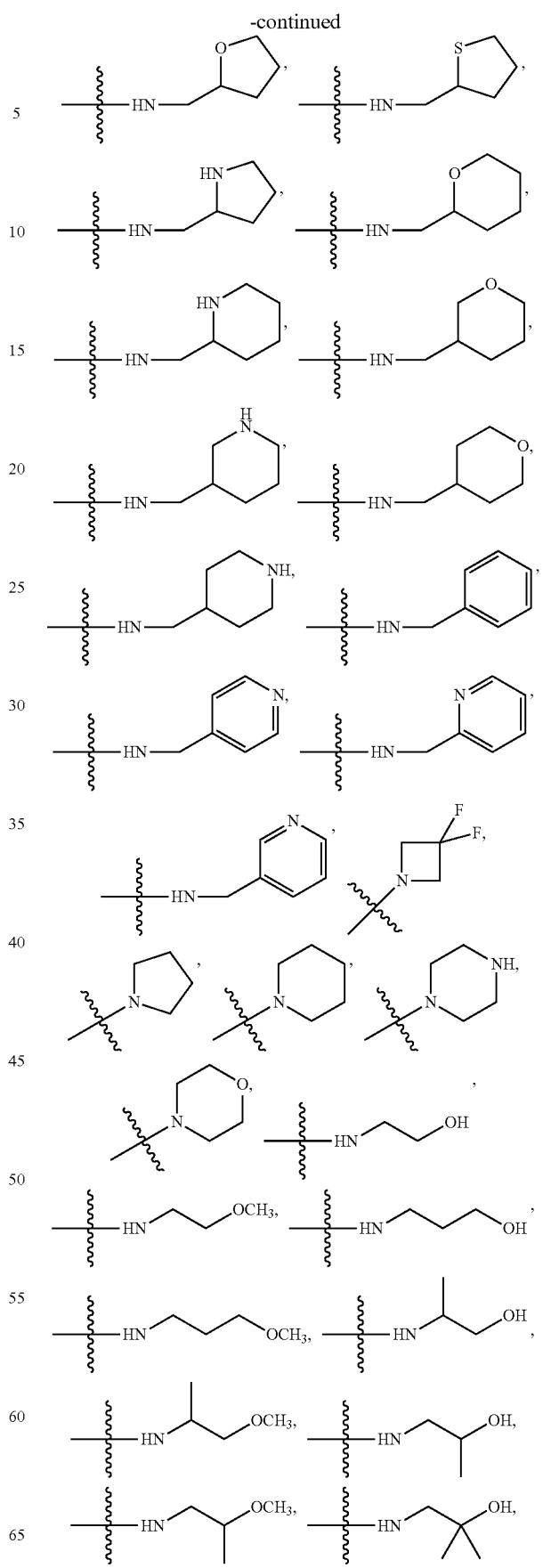

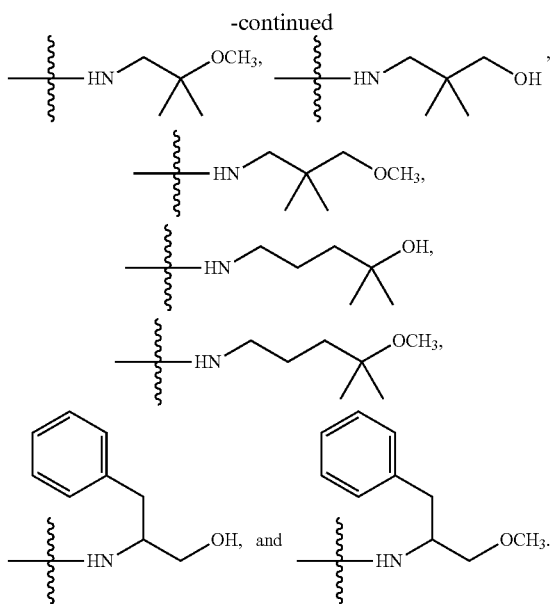

In an alternate embodiment of formula (I), Y is $NR^6C(O)R^7$ or $NR^6SO_2R^7$.

In one embodiment of formula (I), $R^6$ is hydrogen. In another embodiment of formula (I), $R^6$ is an unsubstituted branched or straight chain $C_{1-4}$-alkyl.

In one embodiment of formula (I), $R^7$ is optionally substituted $C_{1-8}$-alkyl. In one embodiment, the $R^7C_{1-8}$-alkyl is unsubstituted. In another embodiment, the $R^7C_{1-8}$-alkyl is substituted with one or two substituents as defined above. Preferably, the one or two substituents are independently selected from the groups consisting of oxo, $-OR^a$, $-NR^bR^c$, $-NR^bC(O)R^a$, $-NHSO_2R^a$, $-SO_2NR^bNR^c$, and benzyl, wherein $R^a$, $R^b$, and $R^c$ are independently selected from the group consisting of H and $C_{1-8}$-alkyl. More preferably, the $R^7C_{1-8}$-alkyl is optionally substituted with one or two substituents selected from the group consisting of hydroxy, methoxy, ethoxy, amino, $-NHCH_3$, $-NHCOCH_3$, $-NHSO_2CH_3$, and $-SO_2NHCH_3$.

In another embodiment of formula (I), $R^7$ is aryl or heteroaryl. In one embodiment of formula (I), $R^7$ is phenyl optionally substituted with one or more $R^5$. In another embodiment of formula (I), $R^7$ is a 5-7-membered heteroaryl optionally substituted with one or more $R^5$. In yet another embodiment, $R^7$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, and more preferably pyridinyl.

In one embodiment of formula (I), $R^7$ is an optionally substituted $C_{3-8}$-cycloalkyl or an optionally substituted heterocycloalkyl. In one embodiment, the $R^7C_{3-8}$-cycloalkyl or heterocycloalkyl is unsubstituted. In another embodiment, the $R^7C_{3-8}$-cycloalkyl or heterocycloalkyl is substituted with one or two $R^5$. Preferably, the one or two substituents are independently selected from the groups consisting of $C_{1-8}$-alkyl, halogen, $-OR^d$, $-NR^eR^f$, $-NR^eC(O)R^d$, $-NHSO_2R^d$, and $-SO_2NR^eNR^f$, wherein $R^d$, $R^e$, and $R^f$ are independently selected from the group consisting of H, $C_{1-8}$-alkyl, $C_{3-8}$-cycloalkyl, 4-7-membered heterocycloalkyl, phenyl, and pyridinyl. More preferably, the $R^7C_{3-8}$-cycloalkyl or heterocycloalkyl is optionally substituted with one or two substituents selected from the group consisting of hydroxy, methoxy, ethoxy, amino, $-NHCH_3$, $-NHCOCH_3$, $-NHSO_2CH_3$, and $-SO_2NHCH_3$.

Where $R^7$ is optionally substituted $C_{3-8}$-cycloalkyl, then preferably $R^7$ is cyclobutyl, cyclopentyl, or cyclohexyl. More preferably, $R^7$ is cyclohexyl.

Where $R^7$ is optionally substituted heterocycloalkyl, then preferably $R^7$ is an optionally substituted 5-7 membered heterocycloalkyl. In another embodiment, the $R^7$ heterocycicoalkyl is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, and 2,6-dioxopiperidinyl. Preferably, $R^7$ is pyrrolidinyl, tetrhydrofuryl, piperidinyl, or tetrahydropyranyl.

In another embodiment of formula (I), $R^7$ is $C_{3-8}$-cycloalkyl-($C_{1-8}$-alkyl), heterocycloalkyl-($C_{1-8}$-alkyl), aryl-($C_{1-8}$-alkyl)-, or heteroaryl-($C_{1-8}$-alkyl), wherein (a) the $R^7$—($C_{1-8}$-alkyl)- is optionally substituted with one or more substituents selected from the group consisting of halogen, cyano, nitro, oxo, $-OR^a$, $-C(O)R^a$, $-C(O)OR^a$, $-OC(O)R^a$, $-NR^bR^c$, $-NR^bC(O)R^a$, $NHC(O)NHR^b$, $-C(O)NR^bR^c$, $-NHSO_2R^a$, $-SO_2NR^bNR^c$, and benzyl; and (b) the $R^7C_{3-8}$-cycloalkyl, heterocycloalkyl, aryl, and heteroaryl are optionally substituted with one or more $R^5$.

In one embodiment, where $R^7$ is $C_{3-8}$-cycloalkyl-($C_{1-8}$-alkyl)-, heterocycloalkyl-($C_{1-8}$-alkyl)-, aryl-($C_{1-8}$-alkyl)-, or heteroaryl-($C_{1-8}$-alkyl), the $R^3$—($C_{1-8}$-alkyl)- is unsubstituted.

In one embodiment, where $R^7$ is $C_{3-8}$-cycloalkyl-($C_{1-8}$-alkyl)-, heterocycloalkyl-($C_{1-8}$-alkyl)-, aryl-($C_{1-8}$-alkyl)-, or heteroaryl-($C_{1-8}$-alkyl), the $R^7$ cycloalkyl, heterocycloalkyl, aryl, or heteroaryl is unsubstituted. In another embodiment, the $R^7$ cycloalkyl, heterocycloalkyl, aryl, or heteroaryl is optionally substituted with one or two $R^5$, wherein the one or two substituents are independently selected from the groups consisting of $C_{1-8}$-alkyl, halogen, $-OR^d$, $-NR^eR^f$, $-NR^eC(O)R^d$, $-NHSO_2R^d$, and $-SO_2NR^eNR^f$, wherein $R^d$, $R^e$, and $R^f$ are independently selected from the group consisting of H, $C_{1-8}$-alkyl, $C_{3-8}$-cycloalkyl, 4-7-membered heterocycloalkyl, phenyl, and pyridinyl. More preferably, the $R^7C_{3-8}$-cycloalkyl or heterocycloalkyl is optionally substituted with one or two substituents selected from the group consisting of hydroxy, methoxy, ethoxy, amino, $-NHCH_3$, $-NHCOCH_3$, $-NHSO_2CH_3$, and $-SO_2NHCH_3$.

Preferably, where $R^7$ is $C_{3-8}$-cycloalkyl-($C_{1-8}$-alkyl)-, heterocycloalkyl-($C_{1-8}$-alkyl)-, aryl-($C_{1-8}$-alkyl)-, or heteroaryl-($C_{1-8}$-alkyl), the —($C_{1-8}$-alkyl)- is —($C_1$-alkyl)-, —($C_2$-alkyl)-, or —($C_3$-alkyl)-, and more preferably —($C_1$-alkyl)-.

In one embodiment, where $R^7$ is $C_{3-8}$-cycloalkyl-($C_{1-8}$-alkyl)-, the $C_{3-8}$-cycloalkyl is optionally substituted cyclobutyl, cyclopentyl, or cyclohexyl.

In one embodiment, where $R^7$ is heterocycloalkyl-($C_{1-8}$-alkyl), the heterocycloalkyl is an optionally substituted 5-7 membered heterocycloalkyl. In another embodiment, the $R^7$ heterocycicoalkyl is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, and preferably pyrrolidinyl, tetrhydrofuryl, piperidinyl, or tetrahydropyranyl.

In one embodiment, where $R^7$ is aryl-($C_{1-8}$-alkyl), the aryl is an optionally substituted phenyl.

In another embodiment, the present invention provides compounds of formula (I) wherein $R^{1a}$ and $R^{1b}$ are hydrogen, X is $CR^2$, $R^2$ is hydrogen, Y is aryl, wherein the aryl is optionally substituted with one, two or three $R^5$, wherein $R^5$ is independently selected from the group consisting of $C_{1-8}$-alkyl, chloro, fluoro, cyano, —$OR^d$, —$C(O)OR^d$, —$NR^eR^f$, —$NR^eC(O)R^d$, —$NHSO_2R^e$, —$C(O)NR^eR^f$, —$SO_2NR^eNR^f$, nitro, —$CF_3$, —$CF_2CF_3$, —$OCF_3$, and $OCF_2CF_3$, wherein $R^d$, $R^e$, and $R^f$ are independently selected from the group consisting of hydrogen, $C_{1-8}$-alkyl, phenyl, $C_{3-8}$-cycloalkyl, 4-7-membered heterocycloalkyl, and pyridyl.

In another embodiment, the present invention provides compounds of formula (I) wherein $R^{1a}$ and $R^{1b}$ are hydrogen, X is N, Y is aryl, wherein the aryl is optionally substituted with one, two, or three $R^5$, wherein $R^5$ is independently selected from the group consisting of $C_{1-8}$-alkyl, chloro, fluoro, cyano, —$OR^d$, —$C(O)OR^d$, —$NR^eR^f$, —$NR^eC(O)R^d$, —$NHSO_2R^e$, —$C(O)NR^eR^f$, —$SO_2NR^eNR^f$, nitro, —$CF_3$, —$CF_2CF_3$, —$OCF_3$, and —$OCF_2CF_3$, wherein $R^d$, $R^e$, and $R^f$ are independently selected from the group consisting of hydrogen, $C_{1-8}$-alkyl, phenyl, $C_{3-8}$-cycloalkyl, 4-7-membered heterocycloalkyl, and pyridyl.

In an alternative embodiment, the present invention provides compounds of formula (I) wherein $R^{1a}$ and $R^{1b}$ are hydrogen, X is $CR^2$, $R^2$ is hydrogen, Y is $NR^3R^4$, wherein $R^3$ is $C_{1-8}$-alkyl, wherein the $C_{1-8}$-alkyl is optionally substituted one or two substituents independently selected from the group consisting of oxo, —$OR^a$, —$NR^bR^c$, —$NR^bC(O)R^a$, and benzyl, wherein Z is a bond, wherein $R^4$ is hydrogen, and wherein $R^a$, $R^b$, and $R^c$ are independently selected from the group consisting of hydrogen, $C_{1-8}$-alkyl, phenyl, $C_{3-8}$-cycloalkyl, 4-7-membered heterocycloalkyl, and pyridyl.

In another embodiment, the present invention provides compounds of formula (I) wherein $R^{1a}$ and $R^{1b}$ are hydrogen, X is N, Y is $NR^3R^4$, wherein $R^3$ is $C_{1-8}$-alkyl, wherein the $C_{1-8}$-alkyl is optionally substituted one or two substituents independently selected from the group consisting of oxo, —$OR^a$, —$NR^bR^c$, —$NR^bC(O)R^a$, and benzyl, wherein Z is a bond, wherein $R^4$ is hydrogen, and wherein $R^a$, $R^b$, and $R^c$ are independently selected from the group consisting of hydrogen, $C_{1-8}$-alkyl, phenyl, $C_{3-8}$-cycloalkyl, 4-7-membered heterocycloalkyl, and pyridyl.

In an alternative embodiment, the present invention provides compounds of formula (I) wherein $R^{1a}$ and $R^{1b}$ are hydrogen, X is $CR^2$, $R^2$ is hydrogen, Y is $NR^3R^4$, wherein $R^3$ is $C_{3-8}$-cycloalkyl, wherein the $C_{3-8}$-cycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^4$ is hydrogen, and wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl.

In another embodiment, the present invention provides compounds of formula (I) wherein $R^{1a}$ and $R^{1b}$ are hydrogen, X is N, Y is $NR^3R^4$, wherein $R^3$ is $C_{3-8}$-cycloalkyl, wherein the $C_{3-8}$-cycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein $R^4$ is hydrogen, wherein Z is a bond, and wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl.

In an alternative embodiment, the present invention provides compounds of formula (I) wherein $R^{1a}$ and $R^{1b}$ are hydrogen, X is $CR^2$, $R^2$ is hydrogen, Y is $NR^3R^4$, wherein $R^3$ is heterocycloalkyl, wherein the heterocycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, $C_{3-8}$-cycloalkyl, 4-7-membered heterocycloalkyl, phenyl, and pyridinyl, and wherein $R^4$ is hydrogen.

In another embodiment, the present invention provides compounds of formula (I) wherein $R^{1a}$ and $R^{1b}$ are hydrogen, X is N, Y is $NR^3R^4$, wherein $R^3$ is heterocycloalkyl, wherein the heterocycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl, and wherein $R^4$ is hydrogen.

In an alternative embodiment, the present invention provides compounds of formula (I) wherein $R^{1a}$ and $R^{1b}$ are hydrogen, X is $CR^2$, $R^2$ is hydrogen, Y is $NR^3R^4$, wherein $R^3$ is $C_{3-8}$-cycloalkyl-($C_{1-8}$-alkyl), wherein the $R^3$—($C_{1-8}$-alkyl)- is unsubstituted, wherein the $R^3C_{3-8}$-cycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl, and wherein $R^4$ is hydrogen.

In another embodiment, the present invention provides compounds of formula (I) wherein $R^{1a}$ and $R^{1b}$ are hydrogen, X is N, Y is $NR^3R^4$, wherein $R^3$ is $C_{3-8}$-cycloalkyl-($C_{1-8}$-alkyl)-, wherein the $R^3$—($C_{1-8}$-alkyl)- is unsubstituted, wherein the $R^3C_{3-8}$-cycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, $C_{3-8}$-cycloalkyl, 4-7-membered heterocycloalkyl, phenyl, and pyridinyl, and wherein $R^4$ is hydrogen.

In an alternative embodiment, the present invention provides compounds of formula (I) wherein $R^{1a}$ and $R^{1b}$ are hydrogen, X is $CR^2$, $R^2$ is hydrogen, Y is $NR^3R^4$, wherein $R^3$ is heterocycloalkyl-($C_{1-8}$-alkyl)-, wherein the $R^3$—($C_{1-8}$-alkyl)- is unsubstituted, wherein the $R^3$ heterocycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl, and wherein $R^4$ is hydrogen.

In another embodiment, the present invention provides compounds of formula (I) wherein $R^{1a}$ and $R^{1b}$ are hydrogen, X is N, Y is $NR^3R^4$, wherein $R^3$ is heterocycloalkyl-($C_{1-8}$-alkyl)-, wherein the $R^3$—($C_{1-8}$-alkyl)- is unsubstituted, wherein the $R^3$ heterocycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl, and wherein $R^4$ is hydrogen.

In an alternative embodiment, the present invention provides compounds of formula (I) wherein $R^{1a}$ and $R^{1b}$ are hydrogen, X is $CR^2$, $R^2$ is hydrogen, Y is $NR^3R^4$, wherein $R^3$ is aryl-($C_{1-8}$-alkyl), wherein the $R^3$—($C_{1-8}$-alkyl)- is unsubstituted, wherein the $R^3$ aryl is optionally substituted with one or two substituents independently selected from the group consisting of $C_{1-8}$-alkyl, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl, and wherein $R^4$ is hydrogen.

In another embodiment, the present invention provides compounds of formula (I) wherein $R^{1a}$ and $R^{1b}$ are hydrogen, X is N, Y is $NR^3R^4$, wherein $R^3$ is aryl-($C_{1-8}$-alkyl), wherein the $R^3$—($C_{1-8}$-alkyl)- is unsubstituted, wherein the $R^3$ aryl is optionally substituted with one or two substituents independently selected from the group consisting of $C_{1-8}$-alkyl, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl, and wherein $R^4$ is hydrogen.

In an alternative embodiment, the present invention provides compounds of formula (I) wherein $R^{1a}$ and $R^{1b}$ are hydrogen, X is $CR^2$, $R^2$ is hydrogen, Y is $NR^3R^4$, wherein $R^3$ is heteroaryl-($C_{1-8}$-alkyl), wherein the $R^3$—($C_{1-8}$-alkyl)- is unsubstituted, wherein the $R^3$ heteroaryl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl, and wherein $R^4$ is hydrogen.

In another embodiment, the present invention provides compounds of formula (I) wherein $R^{1a}$ and $R^{1b}$ are hydrogen, X is N, Y is $NR^3R^4$, wherein $R^3$ is heteroaryl-($C_{1-8}$-alkyl)-, wherein the $R^3$—($C_{1-8}$-alkyl)- is unsubstituted, wherein the $R^3$ heteroaryl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl, and wherein $R^4$ is hydrogen.

In an alternative embodiment, the present invention provides compounds of formula (I) wherein $R^{1a}$ and $R^{1b}$ are hydrogen, X is $CR^2$, $R^2$ is hydrogen, Y is $NR^3R^4$, wherein $R^3$ and $R^4$ are joined together to form a 4-7 membered heterocycloalkyl, wherein the heterocycloalkyl is optionally substituted with one or two substituents selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl.

In another embodiment, the present invention provides compounds of formula (I) wherein $R^{1a}$ and $R^{1b}$ are hydrogen, X is N, Y is $NR^3R^4$, wherein $R^3$ and $R^4$ are joined together to form a 4-7 membered heterocycloalkyl, wherein the heterocycloalkyl is optionally substituted with one or two substituents selected from the group consisting of $C_{1-8}$-alkyl, oxo, cyano, halogen, —$OR^d$, —$NR^eR^f$, —$NR^eC(O)R^d$, and —$NHSO_2R^e$, wherein Z is a bond, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl.

In an alternative embodiment, the present invention provides compounds of formula (I) wherein $R^{1a}$ and $R^{1b}$ are hydrogen, X is $CR^2$, $R^2$ is hydrogen, Y is $NR^6C(O)R^7$ or $NR^6SO_2R^7$, wherein $R^7$ is $C_{1-8}$-alkyl, wherein the $C_{1-8}$-alkyl is optionally substituted one or two substituents independently selected from the group consisting of oxo, —$OR^a$, —$NR^bR^c$, —$NR^bC(O)R^a$, and benzyl, wherein $R^6$ is hydrogen, and wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl.

In another embodiment, the present invention provides compounds of formula (I) wherein $R^{1a}$ and $R^{1b}$ are hydrogen, X is N, Y is $NR^6C(O)R^7$ or $NR^6SO_2R^7$, wherein $R^7$ is $C_{1-8}$-alkyl, wherein the $C_{1-8}$-alkyl is optionally substituted one or two substituents independently selected from the group consisting of oxo, —$OR^a$, —$NR^bR^c$, —$NR^bC(O)R^a$, and benzyl, wherein $R^6$ is hydrogen, and wherein $R^a$, $R^b$, and $R^c$ are independently selected from the group consisting of hydrogen, $C_{1-8}$-alkyl, phenyl, $C_{3-8}$-cycloalkyl, 4-7-membered heterocycloalkyl, and pyridyl.

In an alternative embodiment, the present invention provides compounds of formula (I) wherein $R^{1a}$ and $R^{1b}$ are hydrogen, X is $CR^2$, $R^2$ is hydrogen, Y is $NR^6C(O)R^7$ or $NR^6SO_2R^7$, wherein $R^7$ is $C_{3-8}$-cycloalkyl, wherein the $C_{3-8}$-cycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein $R^6$ is hydrogen, and wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl.

In another embodiment, the present invention provides compounds of formula (I) wherein $R^{1a}$ and $R^{1b}$ are hydrogen, X is N, Y is $NR^6C(O)R^7$ or $NR^6SO_2R^7$, wherein $R^7$ is $C_{3-8}$-cycloalkyl, wherein the $C_{3-8}$-cycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein $R^6$ is hydrogen, and wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl.

In an alternative embodiment, the present invention provides compounds of formula (I) wherein $R^{1a}$ and $R^{1b}$ are hydrogen, X is $CR^2$, $R^2$ is hydrogen, Y is $NR^6C(O)R^7$ or $NR^6SO_2R^7$, wherein $R^7$ is heterocycloalkyl, wherein the heterocycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein $R^d$, $R^e$, and $R^f$ are independently selected from the group consisting of H, $C_{1-8}$-alkyl, $C_{3-8}$-cycloalkyl, 4-7-membered heterocycloalkyl, phenyl, and pyridinyl, and wherein $R^6$ is hydrogen.

In another embodiment, the present invention provides compounds of formula (I) wherein $R^{1a}$ and $R^{1b}$ are hydrogen, X is N, Y is $NR^6C(O)R^7$ or $NR^6SO_2R^7$, wherein $R^7$ is aryl, wherein the aryl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^e$, wherein $R^d$, $R^e$, and $R^f$ are independently selected from the group consisting of H, $C_{1-8}$-alkyl, phenyl, $C_{3-8}$-cycloalkyl, 4-7-membered heterocycloalkyl, and pyridinyl, and wherein $R^6$ is hydrogen.

In an alternative embodiment, the present invention provides compounds of formula (I) wherein $R^{1a}$ and $R^{1b}$ are hydrogen, X is $CR^2$, $R^2$ is hydrogen, Y is $NR^6C(O)R^7$ or $NR^6SO_2R^7$, wherein $R^7$ is aryl, wherein the aryl is optionally substituted with one or two substituents independently selected from the group consisting of $C_{1-8}$-alkyl, oxo, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, C$_{3-8}$-cycloalkyl, 4-7-membered heterocycloalkyl, phenyl, and pyridinyl, and wherein R$^6$ is hydrogen.

In another embodiment, the present invention provides compounds of formula (I) wherein R$^{1a}$ and R$^{1b}$ are hydrogen, X is N, Y is NR$^6$C(O)R$^7$ or NR$^6$SO$_2$R$^7$, wherein R$^7$ is heterocycloalkyl, wherein the heterocycloalkyl is optionally substituted with one or two substituents independently selected from the group consisting of C$_{1-8}$-alkyl, oxo, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, phenyl, C$_{3-8}$-cycloalkyl, 4-7-membered heterocycloalkyl, and pyridinyl, and wherein R$^6$ is hydrogen.

In an alternative embodiment, the present invention provides compounds of formula (I) wherein R$^{1a}$ and R$^{1b}$ are hydrogen, X is CR$^2$, R$^2$ is hydrogen, Y is NR$^6$C(O)R$^7$ or NR$^6$SO$_2$R$^7$, wherein R$^7$ is heteroaryl, wherein the heteroaryl is optionally substituted with one or two substituents independently selected from the group consisting of C$_{1-8}$-alkyl, oxo, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, C$_{3-8}$-cycloalkyl, 4-7-membered heterocycloalkyl, phenyl, and pyridinyl, and wherein R$^6$ is hydrogen.

In another embodiment, the present invention provides compounds of formula (I) wherein R$^{1a}$ and R$^{1b}$ are hydrogen, X is N, Y is NR$^6$C(O)R$^7$ or NR$^6$SO$_2$R$^7$, wherein R$^7$ is heteroaryl, wherein the heteroaryl is optionally substituted with one or two substituents independently selected from the group consisting of C$_{1-8}$-alkyl, oxo, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, phenyl, C$_{3-8}$-cycloalkyl, 4-7-membered heterocycloalkyl, and pyridinyl, and wherein R$^6$ is hydrogen.

In an alternative embodiment, the present invention provides compounds of formula (I) wherein R$^{1a}$ and R$^{1b}$ are hydrogen, X is CR$^2$, R$^2$ is hydrogen, Y is NR$^6$C(O)R$^7$ or NR$^6$SO$_2$R$^7$, wherein R$^7$ is C$_{3-8}$-cycloalkyl-(C$_{1-8}$-alkyl)-, wherein the R$^7$—(C$_{1-8}$-alkyl)- is unsubstituted, wherein the R$^7$C$_{3-8}$-cycloalkyl is optionally substituted with one or two substituents independently selected from the group consisting of C$_{1-8}$-alkyl, oxo, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, phenyl, C$_{3-8}$-cycloalkyl, 4-7-membered heterocycloalkyl, and pyridinyl, and wherein R$^6$ is hydrogen.

In another embodiment, the present invention provides compounds of formula (I) wherein R$^{1a}$ and R$^{1b}$ are hydrogen, X is N, Y is NR$^6$C(O)R$^7$ or NR$^6$SO$_2$R$^7$, wherein R$^7$ is C$_{3-8}$-cycloalkyl-(C$_{1-8}$-alkyl)-, wherein the R$^7$—(C$_{1-8}$-alkyl)- is unsubstituted, wherein the R$^7$C$_{3-8}$-cycloalkyl is optionally substituted with one or two substituents independently selected from the group consisting of C$_{1-8}$-alkyl, oxo, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, C$_{3-8}$-cycloalkyl, 4-7-membered heterocycloalkyl, phenyl, and pyridinyl, and wherein R$^6$ is hydrogen.

In an alternative embodiment, the present invention provides compounds of formula (I) wherein R$^{1a}$ and R$^{1b}$ are hydrogen, X is CR$^2$, R$^2$ is hydrogen, Y is NR$^6$C(O)R$^7$ or NR$^6$SO$_2$R$^7$, wherein R$^7$ is heterocycloalkyl-(C$_{1-8}$-alkyl)-, wherein the R$^7$—(C$_{1-8}$-alkyl)- is unsubstituted, wherein the R$^7$ heterocycloalkyl is optionally substituted with one or two substituents independently selected from the group consisting of C$_{1-8}$-alkyl, oxo, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, phenyl, C$_{3-8}$-cycloalkyl, 4-7-membered heterocycloalkyl, and pyridinyl, and wherein R$^6$ is hydrogen.

In another embodiment, the present invention provides compounds of formula (I) wherein R$^{1a}$ and R$^{1b}$ are hydrogen, X is N, Y is NR$^6$C(O)R$^7$ or NR$^6$SO$_2$R$^7$, wherein R$^7$ is heterocycloalkyl-(C$_{1-8}$-alkyl), wherein the R$^7$—(C$_{1-8}$-alkyl)- is unsubstituted, wherein the R$^7$ heterocycloalkyl is optionally substituted with one or two substituents independently selected from the group consisting of C$_{1-8}$-alkyl, oxo, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, phenyl, C$_{3-8}$-cycloalkyl, 4-7-membered heterocycloalkyl, and pyridinyl, and wherein R$^6$ is hydrogen.

In an alternative embodiment, the present invention provides compounds of formula (I) wherein R$^{1a}$ and R$^{1b}$ are hydrogen, X is CR$^2$, R$^2$ is hydrogen, Y is NR$^6$C(O)R$^7$ or NR$^6$SO$_2$R$^7$, wherein R$^7$ is aryl-(C$_{1-8}$-alkyl)-, wherein the R$^7$—(C$_{1-8}$-alkyl)- is unsubstituted, wherein the R$^7$ aryl is optionally substituted with one or two substituents independently selected from the group consisting of C$_{1-8}$-alkyl, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, phenyl, C$_{3-8}$-cycloalkyl, 4-7-membered heterocycloalkyl, and pyridinyl, and wherein R$^6$ is hydrogen.

In another embodiment, the present invention provides compounds of formula (I) wherein R$^{1a}$ and R$^{1b}$ are hydrogen, X is N, Y is NR$^6$C(O)R$^7$ or NR$^6$SO$_2$R$^7$, wherein R$^7$ is aryl-(C$_{1-8}$-alkyl), wherein the R$^7$—(C$_{1-8}$-alkyl)- is unsubstituted, wherein the R$^7$ aryl is optionally substituted with one or two substituents independently selected from the group consisting of C$_{1-8}$-alkyl, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, phenyl, C$_{3-8}$-cycloalkyl, 4-7-membered heteroyclkoalkyl, and pyridinyl, and wherein R$^6$ is hydrogen.

In an alternative embodiment, the present invention provides compounds of formula (I) wherein R$^{1a}$ and R$^{1b}$ are hydrogen, X is CR$^2$, R$^2$ is hydrogen, Y is NR$^6$C(O)R$^7$ or NR$^6$SO$_2$R$^7$, wherein R$^7$ is heteroaryl-(C$_{1-8}$-alkyl), wherein the R$^7$—(C$_{1-8}$-alkyl)- is unsubstituted, wherein the R$^3$ heteroaryl is optionally substituted with one or two substituents independently selected from the group consisting of C$_{1-8}$-alkyl, oxo, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, phenyl, C$_{3-8}$-cycloalkyl, 4-7-membered heterocycloalkyl, and pyridinyl, and wherein R$^6$ is hydrogen.

In another embodiment, the present invention provides compounds of formula (I) wherein R$^{1a}$ and R$^{1b}$ are hydrogen, X is N, Y is NR$^6$C(O)R$^7$ or NR$^6$SO$_2$R$^7$, wherein R$^7$ is heteroaryl-(C$_{1-8}$-alkyl), wherein the R$^7$—(C$_{1-8}$-alkyl)- is unsubstituted, wherein the R$^7$ heteroaryl is optionally substituted with one or two substituents independently selected from the group consisting of C$_{1-8}$-alkyl, oxo, cyano, halogen, —OR$^d$, —NR$^e$R$^f$, —NR$^e$C(O)R$^d$, and —NHSO$_2$R$^e$, wherein R$^d$, R$^e$, and R$^f$ are independently selected from the group consisting of H, C$_{1-8}$-alkyl, phenyl, C$_{3-8}$-cycloalkyl, 4-7-membered heterocycloalkyl, and pyridinyl, and wherein R$^6$ is hydrogen.

Another aspect of the invention provides compounds of formula (II), wherein R$^{1a}$, R$^{1b}$, R$^{1c}$, R$^3$ and R$^4$ are as defined generally and in subsets above.

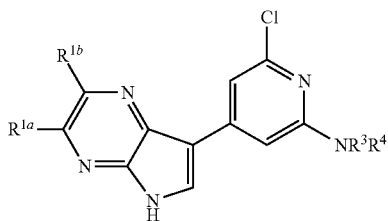

formula (II)

In one embodiment of formula (II), $R^{1a}$ and $R^{1b}$ are hydrogen.

In one embodiment of formula (II), $R^3$ is optionally substituted $C_{1-8}$-alkyl or optionally substituted $C_{2-8}$-alkenyl. In one embodiment, the $R^3C_{1-8}$-alkyl or $C_{2-8}$-alkenyl is unsubstituted. In another embodiment, the $R^3C_{1-8}$-alkyl or $C_{2-8}$-alkenyl is substituted with one or two substituents as defined above. Preferably, the one or two substituents are independently selected from the groups consisting of oxo, —$OR^a$—$NR^bR^c$—$NR^bC(O)R^a$, —$NHSO_2R^a$, —$SO_2NR^bNR^c$, and benzyl, wherein $R^a$, $R^b$, and $R^c$ are independently selected from the group consisting of H and $C_{1-8}$-alkyl. More preferably, the $R^3C_{1-8}$-alkyl or $C_{2-8}$-alkenyl is optionally substituted with one or two substituents selected from the group consisting of hydroxy, methoxy, ethoxy, amino, —$NHCH_3$, —$NHCOCH_3$, —$NHSO_2CH_3$, and —$SO_2NHCH_3$.

Where $R^3$ is optionally substituted $C_{1-8}$-alkyl, then preferably $R^3$ is methyl, ethyl, propyl, isopropyl, n-butyl, sec-butyl, t-butyl, 3-methylbutan-1-yl, pentyl, neopentyl, or 4,4-dimethylpentan-1-yl.

Where $R^3$ is optionally substituted $C_{2-8}$-alkenyl, then preferably $R_3$ is vinyl, prop-2-enyl, or but-3-enyl.

In another embodiment of formula (II), $R^3$ is aryl or heteroaryl. In one embodiment of formula (II), $R^3$ is phenyl optionally substituted with one or more $R^5$. In another embodiment of formula (II), $R^3$ is a 5-7-membered heteroaryl optionally substituted with one or more $R^5$. In yet another embodiment, $R^3$ is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, and more preferably pyridinyl.

In one embodiment of formula (II), $R^3$ is an optionally substituted $C_{3-8}$-cycloalkyl or an optionally substituted heterocycloalkyl. In one embodiment, the $R^3C_{3-8}$-cycloalkyl or heterocycloalkyl is unsubstituted. In another embodiment, the $R^3C_{3-8}$-cycloalkyl or heterocycloalkyl is substituted with one or two $R^5$. Preferably, the one or two substituents are independently selected from the groups consisting of $C_{1-8}$-alkyl, halogen, —$OR^d$, —$NR^eR^f$, —$NR^eC(O)R^d$, —$NHSO_2R^d$, and —$SO_2NR^eNR^f$, wherein $R^d$, $R^e$, and $R^f$ are independently selected from the group consisting of H, $C_{1-8}$-alkyl, $C_{3-8}$-cycloalkyl, 4-7-membered heterocycloalkyl, phenyl, and pyridinyl. More preferably, the $R^3C_{3-8}$-cycloalkyl or heterocycloalkyl is optionally substituted with one or two substituents selected from the group consisting of hydroxy, methoxy, ethoxy, amino, —$NHCH_3$, —$NHCOCH_3$, —$NHSO_2CH_3$, and —$SO_2NHCH_3$.

Where $R^3$ is optionally substituted $C_{3-8}$-cycloalkyl, then preferably $R^3$ is cyclobutyl, cyclopentyl, or cyclohexyl. More preferably, $R^3$ is cyclohexyl.

Where $R^3$ is optionally substituted heterocycloalkyl, then preferably $R^3$ is an optionally substituted 5-7 membered heterocycloalkyl. In another embodiment, the $R^3$ heterocyciocoalkyl is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, and 2,6-dioxopiperidinyl. Preferably, $R^3$ is pyrrolidinyl, tetrhydrofuryl, piperidinyl, or tetrahydropyranyl.

In another embodiment of formula (II), $R^3$ is $C_{3-8}$-cycloalkyl-($C_{1-8}$-alkyl), heterocycloalkyl-($C_{1-8}$-alkyl), aryl-($C_{1-8}$-alkyl)-, or heteroaryl-($C_{1-8}$-alkyl), wherein (a) the $R^3$—($C_{1-8}$-alkyl)- is optionally substituted with one or more substituents selected from the group consisting of halogen, cyano, nitro, oxo, —$OR^a$, —$C(O)R^a$, —$C(O)OR^a$, —$OC(O)R^a$, —$NR^bR^c$, —$NR^bC(O)R^a$, $NHC(O)NHR^b$, —$C(O)NR^bR^c$, —$NHSO_2R^a$, —$SO_2NR^bNR^c$, and benzyl; and (b) the $R^3C_{3-8}$-cycloalkyl, heterocycloalkyl, aryl, and heteroaryl are optionally substituted with one or more $R^5$.

In one embodiment, where $R^3$ is $C_{3-8}$-cycloalkyl-($C_{1-8}$-alkyl)-, heterocycloalkyl-($C_{1-8}$-alkyl)-, aryl-($C_{1-8}$-alkyl), or heteroaryl-($C_{1-8}$-alkyl), the $R^3$—($C_{1-8}$-alkyl)- is unsubstituted.

In one embodiment, where $R^3$ is $C_{3-8}$-cycloalkyl-($C_{1-8}$-alkyl), heterocycloalkyl-($C_{1-8}$-alkyl)-, aryl-($C_{1-8}$-alkyl)-, or heteroaryl-($C_{1-8}$-alkyl), the $R^3$ cycloalkyl, heterocycloalkyl, aryl, or heteroaryl is unsubstituted. In another embodiment, the $R^3$ cycloalkyl, heterocycloalkyl, aryl, or heteroaryl is optionally substituted with one or two $R^5$, wherein the one or two substituents are independently selected from the groups consisting of $C_{1-8}$-alkyl, halogen, —$OR^d$, —$NR^eR^f$, —$NR^eC(O)R^d$, —$NHSO_2R^d$, and —$SO_2NR^eNR^f$, wherein $R^d$, $R^e$, and $R^f$ are independently selected from the group consisting of H, $C_{1-8}$-alkyl, $C_{3-8}$-cycloalkyl, 4-7-membered heterocycloalkyl, phenyl, and pyridinyl. More preferably, the $R^3C_{3-8}$-cycloalkyl or heterocycloalkyl is optionally substituted with one or two substituents selected from the group consisting of hydroxy, methoxy, ethoxy, amino, —$NHCH_3$, —$NHCOCH_3$, —$NHSO_2CH_3$, and —$SO_2NHCH_3$.

Preferably, where $R^3$ is $C_{3-8}$-cycloalkyl-($C_{1-8}$-alkyl)-, heterocycloalkyl-($C_{1-8}$-alkyl)-, aryl-($C_{1-8}$-alkyl), or heteroaryl-($C_{1-8}$-alkyl), the —($C_{1-8}$-alkyl)- is —($C_1$-alkyl)-, —($C_2$-alkyl)-, or —($C_3$-alkyl)-, and more preferably —($C_1$-alkyl)-.

In one embodiment, where $R^3$ is $C_{3-8}$-cycloalkyl-($C_{1-8}$-alkyl)-, the $C_{3-8}$-cycloalkyl is optionally substituted cyclobutyl, cyclopentyl, or cyclohexyl.

In one embodiment, where $R^3$ is heterocycloalkyl-($C_{1-8}$-alkyl), the heterocycloalkyl is an optionally substituted 5-7 membered heterocycloalkyl. In another embodiment, the $R^3$ heterocycicoalkyl is pyrrolidinyl, tetrhydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl, and preferably pyrrolidinyl, tetrhydrofuryl, piperidinyl, or tetrahydropyranyl.

In one embodiment, where $R^3$ is aryl-($C_{1-8}$-alkyl), the aryl is an optionally substituted phenyl.

In one embodiment, where $R^3$ is heteroarylaryl-($C_{1-8}$-alkyl), the heteroaryl is an optionally substituted 5-7-membered heteroaryl. In yet another embodiment, the $R^3$ heteroaryl is furanyl, thiophenyl, pyrrolyl, imidazolyl, pyrazolyl, triazolyl, tetrazolyl, oxazolyl, isoxazolyl, thiazolyl, isothiazolyl, thiodiazolyl, oxadiazolyl, pyridinyl, pyridazinyl, pyrimidinyl, or pyrazinyl, and more preferably pyridinyl.

In one embodiment of formula (II), $R^4$ is hydrogen. In another embodiment of formula (II), $R^4$ is an unsubstituted branched or straight chain $C_{1-8}$ alkyl. In yet another embodiment of formula (II), $R^4$ is methyl, ethyl, propyl, isopropyl, n-butyl, sec-butyl, or t-butyl. Where $R^4$ is an unsubstituted branched or straight chain $C_{1-8}$ alkyl, then preferably $R^4$ is methyl. In another embodiment of formula (II), $R^4$ is a substituted branched or straight chain $C_{1-8}$ alkyl, wherein the $C_{1-8}$-alkyl is substituted with —$OR^a$ or —$NR^bR^c$, wherein $R^a$, $R^b$, and $R^c$ are independently selected from the group consisting of H and $C_{1-8}$-alkyl.

In one embodiment of formula (II), $R^3$ and $R^4$ can be joined together to form a heterocycloalkyl ring, wherein the heterocycloalkyl ring is optionally substituted with one or more $R^5$. In another embodiment, $R^3$ and $R^4$ are joined together to form a 4-7 membered heterocycloalkyl, wherein the heterocycloalkyl is unsubstituted or substituted with one or two $R^5$.

Preferably, the one or two substituents independently selected from the groups consisting of $C_{1-8}$-alkyl, halogen, —$OR^d$, —$NR^eR^f$, —$NR^eC(O)R^d$, —$NHSO_2R^d$, and —$SO_2NR^eNR^f$, wherein $R^d$, $R^e$, and $R^f$ are independently selected from the group consisting of H, $C_{1-8}$-alkyl, $C_{3-8}$-cycloalkyl, 4-7-membered heterocycloalkyl, phenyl, and pyridinyl. More preferably, the heterocycloalkyl is optionally substituted with one or two substituents selected from the group consisting of hydroxy, methoxy, ethoxy, amino, —$NHCH_3$, —$NHCOCH_3$, —$NHSO_2CH_3$, and —$SO_2NHCH_3$.

In one embodiment for formula (II) where $R^3$ and $R^4$ are joined together to form a 4-7 membered heterocycloalkyl, the heterocycloalkyl is azetidinyl, pyrrolidinyl, imidazolidinyl, pyrazolidinyl, piperidinyl, piperazinyl, morpholinyl, 2-oxopyrrolidinyl, 2,5-dioxopyrrolidinyl, 2-oxopiperidinyl, 4-oxopiperidinyl, or 2,6-dioxopiperidinyl, and preferably pyrrolidinyl, tetrahydrofuryl, piperidinyl, or tetrahydropyranyl.

Specific embodiments contemplated as part of the invention include, but are not limited to, compounds of formula (I), for example:

6-chloro-N-cyclohexyl-4-(5H-pyrrolo[3,2-b]pyrazin-7-yl)pyridin-2-amine;
Trans 4-(6-chloro-4-(5H-pyrrolo[3,2-b]pyrazin-7-yl)pyridin-2-ylamino)cyclohexanol;
6-chloro-N-(piperidin-3-yl)-4-(5H-pyrrolo[2,3-b]pyrazin-7-yl)pyridin-2-amine;
6-chloro-N-(1-ethylpiperidin-3-yl)-4-(5H-pyrrolo[2,3-b]pyrazin-7-yl)pyridin-2-amine;
(3-(6-chloro-4-(5H-pyrrolo[2,3-b]pyrazin-7-yl)pyridin-2-ylamino)piperidin-1-yl)(cyclopropyl)methanone;
6-chloro-N-(1-(methylsulfonyl)piperidin-3-yl)-4-(5H-pyrrolo[2,3-b]pyrazin-7-yl)pyridin-2-amine;
Trans $N^1$-(6-chloro-4-(5H-pyrrolo[2,3-b]pyrazin-7-yl)pyridin-2-yl)cyclohexane-1,4-diamine;
N-(trans-4-(6-chloro-4-(5H-pyrrolo[2,3-b]pyrazin-7-yl)pyridin-2-ylamino)cyclohexyl)cyclopropanecarboxamide;
trans-$N^1$-(6-chloro-4-(5H-pyrrolo[2,3-b]pyrazin-7-yl)pyridin-2-yl)-$N^4$,$N^4$-dimethylcyclohexane-1,4-diamine;
6-chloro-N-((1-(methylsulfonyl)piperidin-3-yl)methyl)-4-(5H-pyrrolo[2,3-b]pyrazin-7-yl)pyridin-2-amine;
N-(3-(6-chloro-4-(5H-pyrrolo[2,3-b]pyrazin-7-yl)pyridin-2-ylamino)cyclohexyl)cyclopropanecarboxamide;
$N^1$-(6-chloro-4-(5H-pyrrolo[2,3-b]pyrazin-7-yl)pyridin-2-yl)-$N^3$,$N^3$-dimethylcyclohexane-1,3-diamine;
N-(3-(6-chloro-4-(5H-pyrrolo[2,3-b]pyrazin-7-yl)pyridin-2-ylamino)cyclohexyl)methanesulfonamide;
N-(6-chloro-4-(5H-pyrrolo[2,3-b]pyrazin-7-yl)pyridin-2-yl)pentanamide;
N-(6-chloro-4-(5H-pyrrolo[2,3-b]pyrazin-7-yl)pyridin-2-yl)nicotinamide;
N-(6-chloro-4-(5H-pyrrolo[2,3-b]pyrazin-7-yl)pyridin-2-yl)piperidine-4-carboxamide;
N-(6-chloro-4-(5H-pyrrolo[2,3-b]pyrazin-7-yl)pyridin-2-yl)benzamide;
6-chloro-4-(5H-pyrrolo[2,3-b]pyrazin-7-yl)pyridin-2-amine;
$N^1$-(6-chloro-4-(5H-pyrrolo[2,3-b]pyrazin-7-yl)pyridin-2-yl)-2,2-dimethylpropane-1,3-diamine;
N-(trans 4-(6-chloro-4-(5H-pyrrolo[3,2-b]pyrazin-7-yl)pyridin-2-ylamino)cyclohexyl)-5-oxopyrrolidine-2-carboxamide;
4-chloro-N-cyclohexyl-6-(5H-pyrrolo[3,2-b]pyrazin-7-yl)pyrimidin-2-amine;
N-(trans 4-((6-chloro-4-(5H-pyrrolo[2,3-b]pyrazin-7-yl)pyridin-2-yl)(ethyl)amino)cyclohexyl)cyclopropanecarboxamide;
N-(3-(6-chloro-4-(5H-pyrrolo[2,3-b]pyrazin-7-yl)pyridin-2-ylamino)cyclohexyl)-2-(dimethylamino)acetamide;
N-(3-((6-chloro-4-(5H-pyrrolo[2,3-b]pyrazin-7-yl)pyridin-2-yl)(ethyl)amino)cyclohexyl)-2-(dimethylamino)acetamide;
N-(3-(6-chloro-4-(5H-pyrrolo[2,3-b]pyrazin-7-yl)pyridin-2-ylamino)cyclohexyl)furan-2-sulfonamide;
trans-4-{[6-chloro-4-(5H-pyrrolo[2,3-b]pyrazin-7-yl)pyridin-2-yl]amino}cyclohexanol;
6-chloro-N-(1-methylpiperidin-3-yl)-4-(5H-pyrrolo[2,3-b]pyrazin-7-yl)pyridin-2-amine;
6-chloro-N-[(1-methylpiperidin-3-yl)methyl]-4-(5H-pyrrolo[2,3-b]pyrazin-7-yl)pyridin-2-amine;
N-(trans-4-{[6-chloro-4-(5H-pyrrolo[2,3-b]pyrazin-7-yl)pyridin-2-yl]amino}cyclohexyl)-1-ethylpyrrolidine-3-carboxamide;
(2S)—N-(trans-4-{[6-chloro-4-(5H-pyrrolo[2,3-b]pyrazin-7-yl)pyridin-2-yl]amino}cyclohexyl)azetidine-2-carboxamide;
N-(trans-4-{[6-chloro-4-(5H-pyrrolo[2,3-b]pyrazin-7-yl)pyridin-2-yl]amino}cyclohexyl)-2,6-dioxopiperidine-4-carboxamide;
N-(trans-4-{[6-chloro-4-(5H-pyrrolo[2,3-b]pyrazin-7-yl)pyridin-2-yl]amino}cyclohexyl)-$N^2$,$N^2$-dimethylalaninamide;
4-{[6-chloro-4-(2-chloro-5H-pyrrolo[2,3-b]pyrazin-7-yl)pyridin-2-yl]amino}cyclohexanol;
4-{[4-(2-bromo-5H-pyrrolo[2,3-b]pyrazin-7-yl)-6-chloro-pyridin-2-yl]amino}cyclohexanol;
6-chloro-4-(2-chloro-5H-pyrrolo[2,3-b]pyrazin-7-yl)-N-cyclohexylpyridin-2-amine;
7-[2-chloro-6-(cyclohexylamino)pyridin-4-yl]-5H-pyrrolo[2,3-b]pyrazine-2-carbonitrile;
7-[2-chloro-6-(cyclohexylamino)pyridin-4-yl]-5H-pyrrolo[2,3-b]pyrazine-2-carboxylic acid;
6-chloro-N-cyclohexyl-4-(2-phenyl-5H-pyrrolo[2,3-b]pyrazin-7-yl)pyridin-2-amine;
7-[2-chloro-6-(cyclohexylamino)pyridin-4-yl]-N-phenyl-5H-pyrrolo[2,3-b]pyrazin-2-amine;
7-[2-chloro-6-(cyclohexylamino)pyridin-4-yl]-N-(3-phenylpropyl)-5H-pyrrolo[2,3-b]pyrazin-2-amine;
6-chloro-N-cyclohexyl-4-[2-(pyrazin-2-yl)-5H-pyrrolo[2,3-b]pyrazin-7-yl]pyridin-2-amine;
7-[2-chloro-6-(cyclohexylamino)pyridin-4-yl]-N-{2-methoxy-4-[4-(4-methylpiperazin-1-yl)piperidin-1-yl]phenyl}-5H-pyrrolo[2,3-b]pyrazin-2-amine; or
6-chloro-N-cyclohexyl-4-{2-[(E)-2-(pyridin-4-yl)ethenyl]-5H-pyrrolo[2,3-b]pyrazin-7-yl}pyridin-2-amine Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The present compounds may be prepared by a variety of processes well known for the preparation of compounds of this class. For example, the compounds of formula (I) wherein the groups X, Y, $R^1$, $R^2$, $R^3$, $R^4$, and n have the meanings as set forth in the summary unless otherwise noted, can be synthesized according to the general methods described in Schemes 1-4, using appropriate starting materials by methods generally available to one of ordinary skill in the art.

Abbreviations which have been used in the descriptions of the Schemes and the Examples that follow are: DMF for N,N-dimethylformamide, DMSO for dimethyl sulfoxide, DMSO-$d_6$ for deuteriated dimethyl sulfoxide, DME for dimethoxyethane, dppf for 1,1'-bis(diphenylphosphino)ferrocene, $Et_2O$ for diethyl ether, EtOAc for ethyl acetate, $Et_3N$ for triethylamine, Ts for toluene sulfonyl, and THF for tetrahydrofuran.

Scheme 1

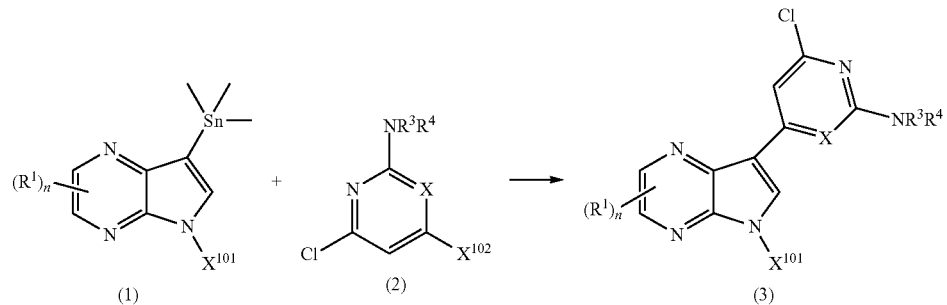

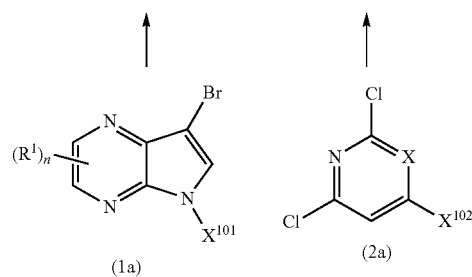

Diazaindoles of formula (I) wherein $X^{101}$ is Ts or benzene sulfonyl can be treated with heteroaryls of formula (2) wherein $X^{102}$ is iodo, bromo, or chloro to provide compounds of general formula (I) wherein Y is $NR^3R^4$ as shown in Scheme 1. This reaction may be performed in the presence of a palladium catalyst and a base at elevated temperature (e.g. at about 70° C. to about 150° C.) and in a suitable solvent such as DMF, dioxane, ethanol, water, DME, or mixtures thereof, optionally in the presence of a ligand such as, but not limited to, tri-o-tolylphosphine, and optionally under microwave irradiation. Non-limiting examples of suitable palladium catalysts include tris(dibenzylideneacetone)dipalladium(0) and bis(tri-tert-butylphosphine)palladium(0). Suitable bases include, but are not limited to, triethylamine, sodium carbonate, potassium acetate, cesium carbonate, and cesium fluoride. In certain cases, the protecting group $X^{101}$ of the diazaindole obtained may be spontaneously removed during the reaction. In other cases, the conversion of compounds of formula (3) wherein $X^{101}$ is Ts or benzene sulfonyl may be converted to compounds of formula (3) wherein $X^{101}$ is hydrogen may be facilitated by treatment of the crude material with potassium hydroxide or sodium hydroxide in dioxane or an alcoholic solvent such as methanol or a mixture of water and methanol, at about room temperature to about reflux temperature of the solvent employed.

Heteroaryls of formula (2) can be prepared by treating (2a) with amines of formula $N(H)R^3R^4$ or salt thereof. The reaction can be conducted in a suitable solvent (e.g. dioxane, DMF, or mixtures thereof) or in excess of the amines employed, at a temperature from about 60° C. to about 150° C., optionally in the presence of a base (e.g. triethylamine, diisopropylethyl amine) and optionally under microwave irradiation.

The diazaindoles of formula (I) can be prepared from the corresponding diazaindoles by (a) brominating the corresponding diazaindoles with a brominating agent such as, but not limited to, N-bromosuccinimide in a suitable solvent (e.g. THF); (2) protecting the product of step (a) with benzenesulfonyl chloride or tosyl chloride, in the presence of a base (e.g. sodium hydride, n-butyl lithium, sodium or potassium hydroxide) and in a suitable solvent (e.g. DMF, THF) to provide compounds of formula (1a); and (3) treating (1a) with hexamethyldistannane in the presence of a palladium catalyst (e.g. tetrakis(triphenylphosphine)palladium(0)) and a base (e.g. potassium acetate), at a temperature from about 70° C. to about 150° C., in a suitable solvent such as toluene, and optionally under microwave irradiation.

Alternatively, compounds of general formula (I) wherein Y is $NR^3R^4$ can be synthesized as shown in Scheme 2.

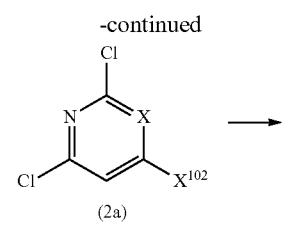

(2a)

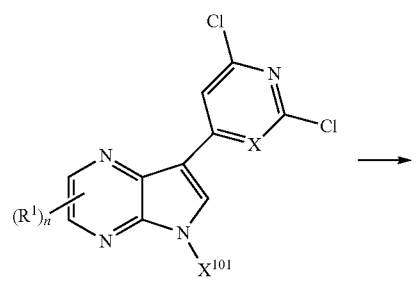

(4)

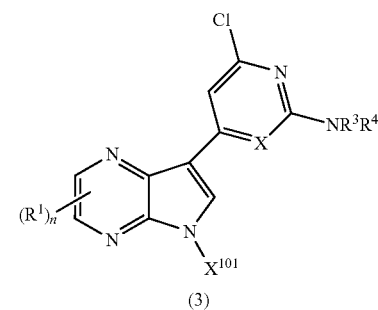

(3)

Compounds of formula (4) can be prepared by treating diazaindoles of formula (I) with heteroaryls of formula (2a) using reaction conditions described for the transformation of (1) to (3) as described in Scheme 1.

Conversion of (4) to amines of formula (3) wherein $X^{101}$ is Ts or benzene sulfonyl can be achieved either by utilizing again the reaction conditions as described for the transformation of (1) to (3), or by direct displacement of the chloro group with amines of formula $N(H)R^3R^4$ employing reaction conditions such as those described for the transformation of (2a) to (2). The protecting group $X^{101}$ can be removed either in situ or by treatment with sodium or potassium hydroxide as described in Scheme 1.

Scheme (3) depicts yet another general procedure for the synthesis of compounds of general formula (I) wherein Y is $NR^3R^4$.

Scheme 2

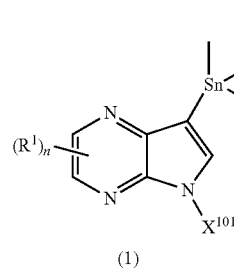

(1)

Scheme 3

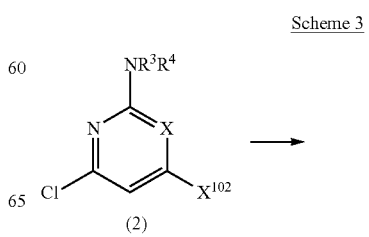

(2)

-continued

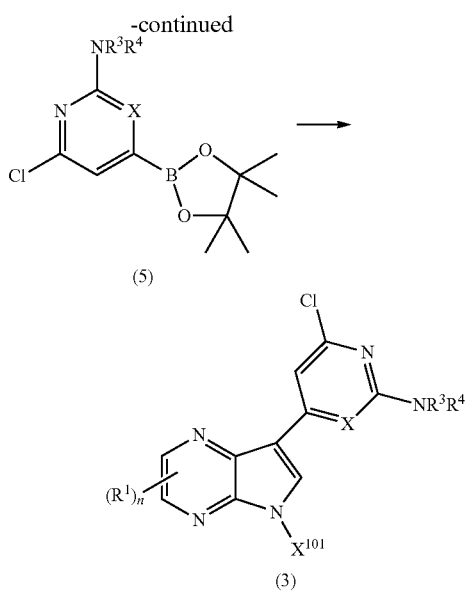

Treatment of compounds of formula (2) with bis(pincolato)diboron in the presence of a palladium catalyst (e.g. dichlorobis (triphenylphosphine) palladium (II), PdCl$_2$ (dppf)) and a base (e.g. sodium carbonate, potassium acetate), at a temperature from about 70° C. to about 150° C., in a suitable solvent such as THF, DMF, dichloromethane, or mixtures thereof, and optionally under microwave irradiation, provides compounds of formula (5).

Coupling of compounds of formula (5) with diazaindoles of formula (1a) to provide compounds of formula (3) wherein $X^{101}$ is hydrogen can be conducted using the above mentioned reaction conditions as described in Scheme 1.

Compounds of general formula (I) wherein Y is N(R$^6$)C(O)R$^7$, R$^6$ is hydrogen or alkyl, and R$^7$ is alkyl, cycloalkyl, heteroaryl, heterocycloalkyl, or aryl, each of which is optionally substituted as described in the Summary, may be prepared utilizing general methods as shown in Scheme 4.

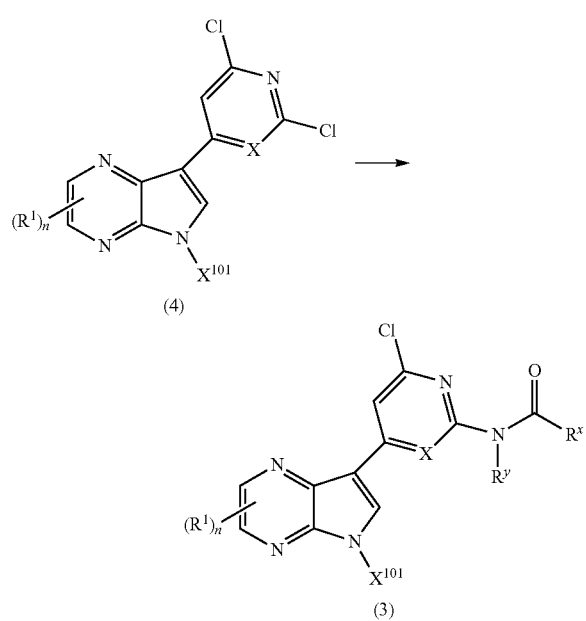

Coupling of compounds of formula (4) wherein $X^{101}$ is Ts or benzene sulfonyl with amides of formula R$^6$C(O)N(H)(R$^7$) in the presence of a palladium catalyst (e.g. palladium acetate (II)), a suitable base (e.g. cesium carbonate), and a ligand (e.g. Xantphos), at a temperature from about 70° C. to about 150° C., and optionally under microwave irradiation, provides compounds of formula (3) wherein X101 is Ts or benzene sulfonyl. The protecting group ($X^{101}$) is either removed in situ during coupling or removed by treatment of the resulting crude material with sodium or potassium hydroxide.

It is appreciated that routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described herein above and in specific examples.

Starting materials, if not commercially available, may be prepared by procedures selected from standard organic chemical techniques (e.g. alkylation, acylation, reductive amination, sulfonylation, oxidation, reduction and the like) that are analogous to the synthesis of known, structurally similar compounds, or techniques that are analogous to the above described schemes or the procedures described in the synthetic examples section.

Unless otherwise noted, microwave reactions described herein were carried out either in a Biotage Initiator 8 or in a CEM Explorer at 200 W.

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperitoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all CDC-7 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having formula (I) are expected to be useful when used with: alkylating agents, angiogenesis inhibitors, antibodies, antimetabolites, antimitotics, antiproliferatives, other apoptosis promoters (for example, Bcl-xL, Bcl-w and Bfl-1) inhibitors, Bcr-Abl kinase inhibitors, BiTE (Bi-Specific T cell Engager) antibodies, aurora kinase inhibitors, biologic response modifiers, cyclin-dependent kinase inhibitors, cell cycle inhibitors, cyclooxygenase-2 inhibitors, DVD's, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAP's) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteosome inhibitors, purine analogs, pyrimidine analogs, receptor tyrosine kinase inhibitors, retinoids/deltoids plant alkaloids, small inhibitory ribonucleic acids (siRNA's), topoisomerase inhibitors, combinations thereof and the like.

A BiTE antibody is a bi-specific antibody that directs T-cells to attach cancer cells by simultaneously binding the two cells. The T-cell then attacks the target cancer cell. Exemplary BiTE antibodies include adecatumumab (Micromet MT201), blinatumomab (Micromet MT103) and the like.

SiRNA's are molecules having endogenous RNA bases or chemically modified nucleotides. The modifications shall not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides or a combination thereof. The siRNA can have varying lengths (10-200 bps) and structures (hairpins, single/double strands, bulges, nicks/gaps, mismatches) and processed in the cell to provide active gene silencing. In certain embodiments, a double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. The multivalent binding protein is preferably engineered to have the three or more antigen binding sites and is generally not a naturally occurring antibody. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific, i.e., capable of binding one antigen or multispecific, i.e., capable of binding two or more antigens. DVD binding proteins comprising two heavy chain DVD polypeptides and two light chain DVD polypeptides are referred to as DVD Ig. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (metrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribaviran, triapine, trimetrexate, S-1, tiazofurin, tegafur, TS-1, vidarabine, UFT and the like.

Aurora kinase inhibitors include AZD-1152, MLN-8054, VX-680, ABT-348 and the like.

Bcl-2 proteins inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like. Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of apoptosis proteins include ApoMab (a fully human affinity-matured IgG1 monoclonal antibody), antibodies that target TRAIL or death receptors (e.g., pro-apoptotic receptor agonists DR4 and DR5), conatumumab, ETR2-ST01, GDC0145, (lexatumumab), HGS-1029, LBY-135, PRO-1762 and tratuzumab.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, TSP-1 and the like. VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like. Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Compounds of this invention can also be used as radiosensitizeser that enhance the efficacy of radiotherapy. Examples of radiotherapy include external beam radiotherapy, teletherapy, brachtherapy and sealed, unsealed source radiotherapy and the like.

Additionally, compounds having formula (I) may be combined with other chemptherapeutic agents such as ABRAXANE™ (ABI-007), ABT-100 (farnesyl transferase inhibitor), ADVEXIN° (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); 0: Vincristine) (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDA-SIL® (quadrivalent human papillomavirus (Types 6, 11, 16, 18) recombinant vaccine), GASTRIMMUNE®, GENA-SENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

EXAMPLES

Example 1

6-chloro-N-cyclohexyl-4-(5H-pyrrolo[3,2-b]pyrazin-7-yl)pyridin-2-amine

Example 1A 6-chloro-N-cyclohexyl-4-iodopyridin-2-amine

A mixture of 2,6-dichloro-4-iodopyridine (5 g, 18.3 mmol) and cyclohexylamine (18.1 g, 183 mmol) was heated in a Biotage Initiator microwave at 150° C. for 30 min. Ethyl acetate (150 mL) was added and the mixture washed with water (100 mL) and brine (50 mL). The organics were concentrated and the residual oil purified by flash chromatography on silica gel eluting with 10% ethyl acetate in hexanes to provide the title compound. Yield: 4.7 g (76%). MS (DCI/NH$_3$) m/z 337 (M+H)$^+$.

Example 1B 6-chloro-N-cyclohexyl-4-(4,4,5,5-tetramethyl-1,3,2-dioxaborolan-2-yl)pyridin-2-amine A solution of EXAMPLE 1A (2.4 g, 7.13 mmol), 4,4,4',4',5,5,5',5'-octamethyl-2,2'-bi(1,3,2-dioxaborolane) (2.72 g, 10.7 mmol), [1,1'-bis(diphenylphosphino)-ferrocene]dichloropalladium(II)adduct with dichloromethane (291 mg, 0.397 mmol) and potassium acetate (1.05 g, 10.7 mmol) in N,N-dimethylformamide (DMF, 30 mL) was heated at 90° C. for 3 h. After cooling, diethyl ether was added and the mixture washed with water (100 mL) and brine (50 mL). The organics were concentrated and the residual oil purified by flash chromatography on silica gel eluting with 10% ethyl acetate in hexanes to provide the title compound. Yield: 2.3 g (96%). MS (DCI/NH$_3$) m/z 337 (M+H)$^+$.

Example 1C 7-bromo-5-(phenylsulfonyl)-5H-pyrrolo[2,3-b]pyrazine

To a solution of 5-bromo-7H-pyrrolo-[2,3-d]pyridine (Ark Pharm, Inc., 2.14 g, 10.81 mmol) in N,N-dimethylformamide (20 mL) at 0° C. was added sodium hydroxide (519 mg, 12.97 mmol) and stirred for 20 min. Benzenesulfonyl chloride (1.46 mL, 11.35 mmol) was added, and the reaction mixture was warmed to ambient temperature and stirred for 3 h. After quenching with water, the precipitated solid was filtered and dried to provide the title compound. Yield: 2.92 g, (80%). MS (DCI/NH$_3$) m/z 339 (M+H)$^+$.

Example 1D 6-chloro-N-cyclohexyl-4-(5H-pyrrolo[3,2-b]pyrazin-7-yl)pyridin-2-amine To a suspension of EXAMPLE 1B (119 mg, 0.36 mmol), EXAMPLE 1C (100 mg, 0.3 mmol), and [1,1'-bis(diphenylphosphino)-ferrocene]dichloropalladium(II)adduct with dichloromethane (49 mg, 0.06 mmol) in 3 mL of a mixture of 7:3:2 dimethoxyethane/water/ethanol was added aqueous sodium carbonate (2M solution, 0.18 mL, 0.36 mmol). The reaction mixture was heated in a Biotage Initiator microwave at 150° C. for 20 min. After cooling, the mixture was concentrated and the residue purified by flash chromatography on silica gel eluting with 5% methanol in dichloromethane to provide the title compound. This was further purified by HPLC (Zorbax C-18, 0.1% trifluoroacetic acid/acetonitrile/water) to yield the title compound. Yield 11 mg (11%). MS (DCI/NH$_3$) m/z 328 (M+H)$^+$; $^1$H NMR (300 MHz, DMSO-d$_6$): 1.13-1.41 (m, 5H), 1.54-1.65 (m, 1H), 1.68-1.80 (m, 2H), 1.86-1.99 (m, 2H), 3.60-3.74 (m, 1H), 6.89 (s, 1H), 7.23 (s, 1H), 7.44 (s, 1H), 8.34 (d, J=2.78 Hz, 1H), 8.52 (d, J=2.78 Hz, 1H), 8.57 (d, J=3.17 Hz, 1H), 12.52 (s, 1H).

Example 2

Trans 4-(6-chloro-4-(5H-pyrrolo[3,2-b]pyrazin-7-yl)pyridin-2-ylamino)cyclohexanol Example 2A Trans 4-(6-chloro-4-iodopyridin-2-ylamino)cyclohexanol A suspension of 2,6-dichloro-4-iodopyridine (6 g, 21.9 mmol) and trans 4-aminocyclohexanol (5.05 g, 43.8 mmol) in 15 mL of a 1:4 mixture of N,N-dimethylformamide/1,4-dioxane was heated in a Biotage Initiator microwave at 200° C. for 55 min. Ethyl acetate (150 mL) was added and the mixture washed with water (100 mL) and brine (50 mL). The organics were concentrated and the residue purified by flash chromatography on silica gel eluting with 60% ethyl acetate in hexanes to provide the title compound. Yield: 3.8 g (49%). MS (DCI/NH$_3$) m/z 353 (M+H)$^+$.

Example 2B 5-(phenylsulfonyl)-7-(trimethylstannyl)-5H-pyrrolo[2,3-b]pyrazine A flask was charged with EXAMPLE 1C (3.88 g, 11.47 mmol) and tetrakis(triphenylphosphine)palladium(0) (1.33 g, 1.15 mmol) and purged with nitrogen. Anhydrous toluene (30 mL) and hexamethyldistannane (3.57 mL, 17.21 mmol) were added, and the flask was purged with nitrogen again and heated at 115° C. for 4 h. After cooling, the mixture was purified by flash chromatography on silica gel eluting with 30% ethyl acetate in hexanes to provide the title compound. Yield: 4.29 g (89%). MS (DCI/NH$_3$) m/z 423 (M+H)$^+$.

Example 2C

Trans 4-(6-chloro-4-(5H-pyrrolo[3,2-b]pyrazin-7-yl)pyridin-2-ylamino)cyclohexanol To a flask charged with EXAMPLE 2A (3.58 g, 10.16 mmol), EXAMPLE 2B (4.29 g, 10.16 mmol), tris(dibenzylideneacetone)dipalladium(0) (803 mg, 0.88 mmol), tri-o-tolylphosphine (801 mg, 2.63 mmol) under nitrogen was added anhydrous N,N-dimethylformamide (30 mL) and triethylamine (4.25 mL, 30.5 mmol). The flask was purged with nitrogen and heated at 70° C. for 6 h. After cooling, ethyl acetate was added and the mixture washed with water (100 mL) and brine (100 mL). The organics were dried over magnesium sulfate, filtered, and concentrated. The residue was dissolved in dioxane (30 mL) and treated with sodium hydroxide (1.63 g, 40.6 mmol) at 90° C. for 2 h. After cooling, the mixture was concentrated and the residue purified by flash chromatography on silica gel eluting with 20% methanol in dichloromethane to provide the title compound. The resulting material was treated with 1M hydrochloric acid solution in diethyl ether to yield the title compound as the hydrochloride salt. Yield 2.0 g (57%). MS (DCI/NH$_3$) m/z 344 (M+H)$^+$; $^1$H NMR (300 MHz, DMSO-d$_6$): 1.18-1.36 (m, 4H), 1.81-1.97 (m, 4H), 3.38-3.48 (m, 1H), 3.55-3.66 (m, 1H), 6.81 (br s, 1H), 7.24 (s, 1H), 7.44 (s, 1H), 8.34 (d, J=2.38 Hz, 1H), 8.52 (d, J=2.38 Hz, 1H), 8.59 (d, J=3.17 Hz, 1H), 12.54 (s, 1H).

Example 3

6-chloro-N-(piperidin-3-yl)-4-(5H-pyrrolo[2,3-b]pyrazin-7-yl)pyridin-2-amine

Example 3A tert-butyl 3-(6-chloro-4-iodopyridin-2-ylamino)piperidine-1-carboxylate A mixture of 2,6-dichloro-4-iodopyridine (1 g, 3.65 mmol) and tert-butyl 3-aminopiperidine-1-carboxylate (3.66 g, 18 mmol) in a sealed tube was heated at 120° C. for 3 days. After cooling, the mixture was poured into 100 mL of water. The solid was collected by filtration and purified by flash chromatography on silica gel eluting with ethyl acetate to provide 680 mg of the title compound. Yield: 43%. MS (DCI/NH$_3$) m/z 438 (M+H)$^+$.

Example 3B tert-butyl 3-(6-chloro-4-(5-(phenylsulfonyl)-5H-pyrrolo[2,3-b]pyrazin-7-yl)pyridin-2-ylamino)piperidine-1-carboxylate A 100 mL round bottle flask was charged with EXAMPLE 2B (120 mg, 0.28 mmol), EXAMPLE 3A (124 mg, 0.28 mmol), bis(tri-t-butylphosphine)palladium(0) (15 mg, 0.028 mmol) and cesium fluoride (22 mg, 0.14 mmol) and purged with nitrogen. Anhydrous dioxane (10 mL) was added via syringe. The solution was purged with nitrogen and heated at 80° C. overnight. After cooling, the mixture was partitioned between ethyl acetate and brine. The organic phase was washed with brine and concentrated. The crude compound was purified by flash chromatography on silica gel eluting with ethyl acetate to provide 100 mg of the title compound. Yield: 62%. MS (DCI/NH$_3$) m/z 570 (M+H)$^+$.

Example 3C 6-chloro-N-(piperidin-3-yl)-4-(5H-pyrrolo[2,3-b]pyrazin-7-yl)pyridin-2-amine A solution of EXAMPLE 3B (100 mg, 0.2 mmol) in dichloromethane (5 mL) was treated with trifluoroacetic acid (1 mL) at ambient temperature for 30 min. The mixture was concentrated and the residue dissolved in ethanol (5 mL). A solution of potassium hydroxide (19 mg, 0.35 mmol) in water (0.2 mL) was added and the solution heated at 50° C. for 3 h. After cooling, the mixture was purified by HPLC (Zorbax, C-18, 250×2.54 column, Mobile phase A: 0.1% trifluoroacetic acid in water; B: 0.1% trifluoroacetic acid in acetonitrile; 0-100% gradient) to yield the title compound as the trifluoroacetate salt. Yield: 30 mg (52%). MS (DCI/NH$_3$) m/z 329 (M+H)$^+$; $^1$H NMR (300 MHz, CD$_3$OD): δ 1.62-1.79 (m, 1H), 1.78-1.98 (m, 1H), 2.01-2.21 (m, 2H), 2.86-3.09 (m, 3H), 3.61 (dd, J=12.21, 3.73 Hz, 1H), 4.12-4.25 (m, 1H), 7.33 (d, J=1.36 Hz, 1H), 7.49 (d, J=1.36 Hz, 1H), 8.28 (s, 1H), 8.30 (d, J=2.37 Hz, 1H), 8.50 (d, J=2.37 Hz, 1H).

Example 4

6-chloro-N-(1-ethylpiperidin-3-yl)-4-(5H-pyrrolo[2,3-b]pyrazin-7-yl)pyridin-2-amine The trifluoroacetate salt of the title compound was isolated as a byproduct in the synthesis of EXAMPLE 3. Yield: 15 mg (24%). MS (DCI/NH$_3$) m/z 357 (M+H)$^+$; $^1$H NMR (300 MHz, CD$_3$OD): δ 1.37 (t, J=7.46 Hz, 3H), 1.51-1.68 (m, 1H), 1.79-2.04 (m, 1H), 2.05-2.23 (m, 2H), 2.62 (t, J=11.36 Hz, 1H), 2.82-3.23 (m, 2H), 3.23 (q, J=7.46 Hz, 2H), 3.48-3.64 (m, 1H), 4.17-4.31 (m, 1H), 7.33 (d, J=1.02 Hz, 1H), 7.48 (d, J=1.36 Hz, 1H), 8.28 (s, 1H), 8.29 (d, J=2.71 Hz, 1H), 8.49 (d, J=2.71 Hz, 1H).

Example 5

(3-(6-chloro-4-(5H-pyrrolo[2,3-b]pyrazin-7-yl)pyridin-2-ylamino)piperidin-1-yl)(cyclopropyl)methanone To a solution of EXAMPLE 3C (20 mg, 0.061 mmol) in anhydrous N,N-dimethylformamide (1 mL) was added cyclopropane carboxylic acid (7 mg, 0.073 mmol), 1-ethyl-3-[3-dimethylaminopropyl]carbodiimide hydrochloride (EDC, 14 mg, 0.073 mmol), 1-hydroxybenzotriazole monohydrate (HOBT, 11 mg, 0.073 mmol) and triethylamine (6 mg, 0.061 mmol). The mixture was stirred at ambient temperature overnight and the crude compound purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt. Yield: 18 mg (75%). MS (DCI/NH$_3$) m/z 397 (M+H)$^+$; $^1$H NMR (300 MHz, CD$_3$OD): δ 0.61-0.73 (m, 1H), 0.73-0.86 (m, 2H), 0.86-0.97 (m, 2H), 1.52-1.76 (m, 2H), 1.78-1.96 (m, 1H), 2.04-2.19 (m, 2H), 2.93-3.22 (m, 1H), 3.75-3.93 (m, 1H), 3.96-4.10 (m, 1H), 4.32-4.50 (m, 1H), 7.30 (s, 1H), 7.44 (s, 1H), 8.27 (s, 1H), 8.29 (d, J=2.37 Hz, 1H), 8.50 (d, J=2.71 Hz, 1H).

Example 6

6-chloro-N-(1-(methylsulfonyl)piperidin-3-yl)-4-(5H-pyrrolo[2,3-b]pyrazin-7-yl)pyridin-2-amine Example 6A 1-(methylsulfonyl)piperidin-3-amine Step A To a solution of tert-butyl piperidin-3-ylcarbamate (1.5 g, 7.5 mmol) in pyridine (20 mL) was added methanesulfonyl chloride (1.0 g, 9 mmol). The mixture was stirred at ambient temperature for 5 h and partitioned between ethyl acetate and brine. The organic phase was washed with brine and concentrated. The residue was purified by flash chromatography on silica gel eluting with ethyl acetate to provide the BOC-protected intermediate.

Step B

The product from STEP A was dissolved in dichloromethane (150 mL), and treated with trifluoroacetic acid (5 mL) at ambient temperature overnight. Concentration afforded the title compound as the trifluoroacetate salt. Yield: 1.1 g (82%). MS (DCI/NH$_3$) m/z 179 (M+H)$^+$.

Example 6B 6-chloro-4-iodo-N-(1-(methylsulfonyl)piperidin-3-yl)pyridin-2-amine

A mixture of 2,6-dichloro-4-iodopyridine (500 mg, 1.8 mmol) and EXAMPLE 6A (976 mg, 5.5 mmol) in ethanol (2 mL) was heated in a Biotage Initiator microwave reactor at 180° C. for 2 h. After cooling, the mixture was partitioned between ethyl acetate and brine. The organic phase was washed with brine and concentrated. The residue was purified by flash chromatography on silica gel eluting with 30% ethyl acetate in hexanes to give the title compound. Yield: 150 mg (20%). MS (DCI/NH$_3$) m/z 416 (M+H)$^+$.

Example 6C 6-chloro-N-(1-(methylsulfonyl)piperidin-3-yl)-4-(5H-pyrrolo[2,3-b]pyrazin-7-yl)pyridin-2-amine A round bottom flask was charged with EXAMPLE 6B (80 mg, 0.2 mmol), EXAMPLE 2B (89 mg, 0.21 mmol), bis(tri-t-butylphosphine)palladium(0) (10 mg, 0.02 mmol) and CsF (29 mg, 0.19 mmol) and purged with nitrogen. Anhydrous dioxane (10 mL) was added and the solution purged with nitrogen and heated at 80° C. overnight. After cooling, the mixture was partitioned between ethyl acetate and brine. The organic phase was washed with brine and concentrated. The residue was purified by flash chromatography on silica gel eluting with 70% ethyl acetate in hexanes. The compound was dissolved in 2 mL of ethanol and treated with potassium hydroxide (45 mg, 0.8 mmol) in water (0.2 mL) at 50° C. for 2 h. After cooling, the mixture was diluted with 10 mL of ethyl acetate. The compound was collected by filtration and washed with ethyl acetate to provide 25 mg of the title compound. Yield: 32%. MS (DCI/NH$_3$) m/z 407 (M+H)$^+$; $^1$H NMR (300 MHz, DMSO-d$_6$): δ 1.35-1.55 (m, 1H), 1.52-1.71 (m, 1H), 1.76-1.97 (m, 2H), 2.54-2.69 (m, 1H), 2.74-2.86 (m, 1H), 2.88 (s, 3H), 3.33-3.47 (m, 1H), 3.57-3.75 (m, 1H), 3.79-3.99 (m, 1H), 7.06 (d, J=7.46 Hz, 1H), 7.30 (d, J=1.02 Hz, 1H), 7.55 (d, J=1.02 Hz, 1H), 8.33 (d, J=2.71 Hz, 1H), 8.51 (d, J=2.71 Hz, 1H), 8.59 (s, 1H), 12.54 (s, 1H).

Example 7

Trans N$^1$-(6-chloro-4-(5H-pyrrolo[2,3-b]pyrazin-7-yl)pyridin-2-yl)cyclohexane-1,4-diamine Example 7A trans N$^1$-(6-chloro-4-iodopyridin-2-yl)cyclohexane-1,4-diamine A mixture of 2,6-dichloro-4-iodopyridine (1 g, 3.65 mmol) and trans-cyclohexane-1,4-diamine (2 g, 18 mmol) in ethanol (2 mL) was heated in a Biotage Initiator microwave reactor at 180° C. for 4 h. After cooling, the mixture was poured into water and the solid collected by filtration and washed with water to give the title compound. Yield: 1.02 g (79%). MS (DCI/NH$_3$) m/z 352 (M+H)$^+$.

Example 7B trans N$^1$-(6-chloro-4-(5H-pyrrolo[2,3-b]pyrazin-7-yl)pyridin-2-yl)cyclohexane-1,4-diamine The title compound was prepared according to the procedure for EXAMPLE 6C, substituting EXAMPLE 7A for EXAMPLE 6B. The material was purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt. Yield: 30 mg (57%). MS (DCI/NH$_3$) m/z 343 (M+H)$^+$; $^1$H NMR (300 MHz, CD$_3$OD): δ 1.27-1.47 (m, 2H), 1.50-1.67 (m, 2H), 2.10 (dd, J=12.37, 1.86 Hz, 2H), 2.22 (dd, J=13.39, 3.56 Hz, 2H), 3.03-3.20 (m, 1H), 3.68-3.90 (m, 1H), 7.25 (d, J=1.36 Hz, 1H), 7.40 (d, J=1.02 Hz, 1H), 8.28 (s, 1H), 8.29 (d, J=2.71 Hz, 1H), 8.49 (d, J=2.71 Hz, 1H).

Example 8

N-(trans-4-(6-chloro-4-(5H-pyrrolo[2,3-b]pyrazin-7-yl)pyridin-2-ylamino)cyclohexyl)cyclopropanecarboxamide Example 8A N-(trans-4-(6-chloro-4-iodopyridin-2-ylamino)cyclohexyl)cyclopropanecarboxamide The title compound was prepared according to the procedure for EXAMPLE 5, substituting EXAMPLE 7A for EXAMPLE 3C. The crude compound was purified by flash chromatography on silica gel eluting with ethyl acetate to provide 130 mg of the title compound. Yield: 78%. MS (DCI/NH$_3$) m/z 420 (M+H)$^+$.

Example 8B

N-(trans-4-(6-chloro-4-(5H-pyrrolo[2,3-b]pyrazin-7-yl)pyridin-2-ylamino)cyclohexyl)cyclopropanecarboxamide The title compound was prepared according to the procedure for EXAMPLE 6C, substituting EXAMPLE 8A for EXAMPLE 6B. Yield: 45 mg (37%). MS (DCI/NH$_3$) m/z 411 (M+H)$^+$; $^1$H NMR (300 MHz, DMSO-d$_6$): δ 0.55-0.71 (m, 4H), 1.21-1.37 (m, 4H), 1.44-1.59 (m, 1H), 1.82 (d, J=2.38 Hz, 2H), 1.92-2.06 (m, 2H), 3.15-3.31 (m, 1H), 3.45-3.71 (m, 1H), 6.87 (d, J=7.93 Hz, 1H), 7.24 (s, 1H), 7.45 (s, 1H), 7.95 (d, J=7.54 Hz, 1H), 8.33 (d, J=2.38 Hz, 1H), 8.51 (d, J=2.38 Hz, 1H), 8.58 (s, 1H), 12.53 (s, 1H).

Example 9 trans-N$^1$-(6-chloro-4-(5H-pyrrolo[2,3-b]pyrazin-7-yl)pyridin-2-yl)-N$^4$,N$^4$-dimethylcyclohexane-1,4-diamine

Example 9A trans-N$^1$-(6-chloro-4-iodopyridin-2-yl)-N4,N4-dimethylcyclohexane-1,4-diamine To a solution of EXAMPLE 7A (130 mg, 0.37 mmol) in methanol (5 mL) was added formaldehyde (150 mg, 1.8 mmol) at ambient temperature. The solution was stirred at ambient temperature for 10 min and sodium cyanoborohydride (23 mg, 0.37 mmol) and zinc chloride (10 mg, 0.07 mmol) were added. The mixture was stirred at ambient temperature overnight and concentrated. The residue was purified by flash chromatography on silica gel eluting with 10% methanol (with 5% ammonium hydroxide) in dichloromethane to give the title compound. Yield: 130 mg (93%). MS (DCI/NH$_3$) m/z 380 (M+H)$^+$.

Example 9B trans-N$^1$-(6-chloro-4-(5H-pyrrolo[2,3-b]pyrazin-7-yl)pyridin-2-yl)-N$^4$,N$^4$-dimethylcyclohexane-1,4-diamine The title compound was prepared according to the procedure for EXAMPLE 6C, substituting EXAMPLE 9A for EXAMPLE 6B. The crude product was purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt. Yield: 30 mg (23%). MS (DCI/NH$_3$) m/z 371 (M+H)$^+$; $^1$H NMR (300 MHz, DMSO-d$_6$): δ 1.17-1.39 (m, 2H), 1.49-1.68 (m, 2H), 1.92-2.18 (m, 4H), 2.75 (s, 6H), 3.06-3.31 (m, 1H), 3.45-3.63 (m, 1H), 6.98 (s, 1H), 7.24 (s, 1H), 7.50 (s, 1 H), 8.35 (d, J=2.37 Hz, 1H), 8.52 (d, J=2.37 Hz, 1H), 8.59 (d, J=3.05 Hz, 1H), 12.54 (s, 1 H).

Example 10

6-chloro-N-((1-(methylsulfonyl)piperidin-3-yl)methyl)-4-(5H-pyrrolo[2,3-b]pyrazin-7-yl)pyridin-2-amine

Example 10A (1-(methylsulfonyl)piperidin-3-yl)methanamine

The title compound was prepared according to the procedure for EXAMPLE 6A, substituting tert-butyl piperidin-3-ylmethylcarbamate for tert-butyl piperidin-3-ylcarbamate. Yield: 380 mg (42%). MS (DCI/NH$_3$) m/z 193 (M+H)$^+$.

Example 10B 6-chloro-4-iodo-N-((1-(methylsulfonyl)piperidin-3-yl)methyl)pyridin-2-amine The title compound was prepared according to procedure for EXAMPLE 6B, substituting EXAMPLE 10A for EXAMPLE 6A. Yield: 80 mg (51%). MS (DCI/NH$_3$) m/z 430 (M+H)$^+$.

Example 10C 6-chloro-N-((1-(methylsulfonyl)piperidin-3-yl)methyl)-4-(5H-pyrrolo[2,3-b]pyrazin-7-yl)pyridin-2-amine The title compound was prepared according to the procedure for EXAMPLE 6C, substituting EXAMPLE 10B for EXAMPLE 6B. Yield: 20 mg (25%). MS (DCI/NH$_3$) m/z 421 (M+H)$^+$; $^1$H NMR (300 MHz, DMSO-d$_6$): δ 1.02-1.32 (m, 2H), 1.33-1.58 (m, 1H), 1.68-1.96 (m, 2H), 2.49-2.59 (m, 1H), 2.62-2.77 (m, 1H), 2.83 (s, 3H), 3.05-3.28 (m, 2H), 3.40-3.51 (m, 1H), 3.58-3.66 (m, 1H), 7.12 (s, 1H), 7.28 (s, 1H), 7.52 (s, 1H), 8.35 (d, J=2.71 Hz, 1H), 8.53 (d, J=2.37 Hz, 1H), 8.61 (d, J=3.05 Hz, 1H), 12.54 (s, 1H).

Example 11

N-(3-(6-chloro-4-(5H-pyrrolo[2,3-b]pyrazin-7-yl)pyridin-2-ylamino)cyclohexyl)cyclopropanecarboxamide

Example 11A

N$^1$-(6-chloro-4-iodopyridin-2-yl)cyclohexane-1,3-diamine

The title compound was prepared according to procedure for EXAMPLE 7A, substituting cyclohexane-1,3-diamine for trans cyclohexane-1,4-diamine. Yield: 1.1 g (86%). MS (DCI/NH$_3$) m/z 352 (M+H)$^+$;

Example 11B

N-(3-(6-chloro-4-iodopyridin-2-ylamino)cyclohexyl)cyclopropanecarboxamide

The title compound was prepared according to the procedure for EXAMPLE 5, substituting EXAMPLE 11A for EXAMPLE 3C. The crude product was purified by flash chromatography on silica gel eluting with ethyl acetate to provide 100 mg of the title compound. Yield: 84%. MS (DCI/NH$_3$) m/z 420 (M+H)$^+$.

Example 11C

N-(3-(6-chloro-4-(5H-pyrrolo[2,3-b]pyrazin-7-yl)pyridin-2-ylamino)cyclohexyl)cyclopropanecarboxamide The title compound was prepared according to procedure for EXAMPLE 6C, substituting EXAMPLE 11B for EXAMPLE 6B. Yield: 29 mg (27%). MS (DCI/NH$_3$) m/z 411 (M+H)$^+$; $^1$H NMR (300 MHz, DMSO-d$_6$): δ 0.50-0.73 (m, 4H), 0.97-1.22 (m, 3H), 1.25-1.43 (m, 1H), 1.43-1.56 (m, 1H), 1.64-1.84 (m, 2H), 1.83-1.98 (m, 1H), 1.99-2.17 (m, 1H), 3.52-3.79 (m, 2H), 6.80 (d, J=8.14 Hz, 1H), 7.26 (s, 1H), 7.38 (s, 1H), 7.97 (d, J=7.80 Hz, 1H), 8.24 (d, J=2.71 Hz, 1H), 8.40 (d, J=2.37 Hz, 1H), 8.54 (s, 1H), 12.54 (s, 1H).

Example 12

N$^1$-(6-chloro-4-(5H-pyrrolo[2,3-b]pyrazin-7-yl)pyridin-2-yl)-N$^3$,N$^3$-dimethylcyclohexane-1,3-diamine Example 12A N$^1$-(6-chloro-4-iodopyridin-2-yl)-N3,N3-dimethylcyclohexane-1,3-diamine The title compound was prepared according to the procedure for EXAMPLE 9A, substituting EXAMPLE 11A for EXAMPLE 7A. Yield: 100 mg (93%). MS (DCI/NH$_3$) m/z 380 (M+H)$^+$.

Example 12B

N$^1$-(6-chloro-4-(5H-pyrrolo[2,3-b]pyrazin-7-yl)pyridin-2-yl)-N$^3$,N$^3$-dimethylcyclohexane-1,3-diamine The title compound was prepared according to the procedure for EXAMPLE 6C, substituting EXAMPLE 12A for EXAMPLE 6B. The crude product was purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt. Yield: 33 mg (34%). MS (DCI/NH$_3$) m/z 371 (M+H)$^+$; $^1$H NMR (300 MHz, DMSO-d$_6$): δ 1.16-1.37 (m, 2H), 1.36-1.57 (m, 1H), 1.77-2.07 (m, 2H), 2.67-2.81 (m, 3H), 2.94 (s, 3H), 2.98 (s, 3H), 3.23-3.55 (m, 2H), 7.14 (s, 1H), 7.27 (s, 1 H), 7.53 (d, J=8.48 Hz, 1H), 8.35 (s, 1H), 8.53 (d, J=2.71 Hz, 1H), 8.60 (d, J=3.05 Hz, 1H), 12.57 (s, 1H).

Example 13

N-(3-(6-chloro-4-(5H-pyrrolo[2,3-b]pyrazin-7-yl)pyridin-2-ylamino)cyclohexyl)methanesulfonamide Example 13A N-(3-(6-chloro-4-iodopyridin-2-ylamino)cyclohexyl)methanesulfonamide To a solution of EXAMPLE 11A (100 mg, 0.3 mmol) in pyridine (5 mL) was added methanesulfonyl chloride (50 mg, 0.4 mmol). The mixture was stirred at ambient temperature for 5 h and partitioned between ethyl acetate and brine. The organic phase was washed with brine and concentrated. The residue was purified by flash chromatography on silica gel eluting with ethyl acetate to provide the title compound. Yield: 100 mg (82%). MS (DCI/NH$_3$) m/z 430 (M+H)$^+$.

Example 13B

N-(3-(6-chloro-4-(5H-pyrrolo[2,3-b]pyrazin-7-yl)pyridin-2-ylamino)cyclohexyl)methanesulfonamide The title compound was prepared according to procedure for EXAMPLE 6C, substituting EXAMPLE 13A for EXAMPLE 6B. Yield: 20 mg (20%). MS (DCI/NH$_3$) m/z 421 (M+H)$^+$; $^1$H NMR (300 MHz, DMSO-d$_6$): δ 0.99-1.25 (m, 3H), 1.27-1.47 (m, 1H), 1.67-1.79 (m, 1H), 1.83-1.94 (m, 2H), 2.13-2.27 (m, 1H), 2.92 (s, 3H), 3.11-3.35 (m, 1H), 3.59-3.81 (m, 1H), 6.93 (d, J=8.14 Hz, 1H), 7.07 (d, J=7.46 Hz, 1H), 7.26 (s, 1H), 7.44 (s, 1H), 8.33 (d, J=2.71 Hz, 1H), 8.51 (d, J=2.71 Hz, 1H), 8.58 (s, 1H), 12.51 (s, 1H).

Example 14

N-(6-chloro-4-(5H-pyrrolo[2,3-b]pyrazin-7-yl)pyridin-2-yl)pentanamide

Example 14A 7-(2,6-dichloropyridin-4-yl)-5-(phenylsulfonyl)-5H-pyrrolo[2,3-b]pyrazine A mixture of EXAMPLE 2B (1.154 g, 2.73 mmol), 2,6-dichloro-4-iodopyridine (0.824 g, 3.01 mmol), triethylamine (1.14 mL, 8.20 mmol), tris(dibenzylideneacetone)dipalladium(0) (0.175 g, 0.191 mmol), and tri-o-tolylphosphine (0.250 g, 0.820 mmol) in N,N-dimethylformamide (40 mL) was degassed and heated at 90° C. for 3.5 h. After cooling, the mixture was filtered and water added to the filtrate. The resulting precipitate was filtered, washed with water, dried, and purified by flash chromatography on silica gel eluting with a gradient of 97.5:2.5 to 95:5 dichloromethane/ethyl acetate to give 0.796 g (72%) of the title compound.

Example 14B

N-(6-chloro-4-(5H-pyrrolo[2,3-b]pyrazin-7-yl)pyridin-2-yl)pentanamide

A mixture of EXAMPLE 14A (0.050 g, 0.123 mmol), pentanamide (0.016 g, 0.160 mmol), cesium carbonate (0.052 g, 0.160 mmol), palladium (II) acetate (1.385 mg, 6.17 μmol), and 9,9-dimethyl-4,5-bis(diphenylphosphino)xanthene (Xantphos, 5.35 mg, 9.25 μmol) in dioxane (1.2 mL) and N,N-dimethylformamide (0.1 mL) was heated in a Biotage Initiator microwave reactor at 170° C. for 10 min. The solids were filtered and the filtrate concentrated. The residue was suspended in dioxane (1 mL) and treated with 20% sodium hydroxide (0.1 mL). The mixture was heated at 50° C. for 2 h. After cooling, the mixture was concentrated and the residue treated with water, sonicated, filtered, and purified by reversed-phase HPLC (Zorbax RX-C18 column (250×21.2 mm, 7 μm particle size) using a gradient of 10% to 100% acetonitrile: 0.1% aqueous trifluoroacetic acid over 40 min at a flow rate of 15 mL/minute) to give 4.2 mg of the title compound as the trifluoroacetate salt. $^1$H NMR (500 MHz, DMSO-D$_6$) 0.89 (t, J=7.3 Hz, 3H), 1.25-1.36 (m, 2H), 1.50-

1.62 (m, 2H), 2.40 (t, J=7.5 Hz, 2H), 8.00 (s, 1H), 8.36 (d, J=2.4 Hz, 1H), 8.57 (d, J=2.4 Hz, 1H), 8.67 (d, J=3.4 Hz, 1H), 8.95 (s, 1H), 10.61 (s, 1H), 12.70 (s, 1H). MS (ESI) m/z 330.5 (M+H)$^+$.

Example 15

N-(6-chloro-4-(5H-pyrrolo[2,3-b]pyrazin-7-yl)pyridin-2-yl)nicotinamide

A mixture of EXAMPLE 14A (0.100 g, 0.247 mmol), nicotinamide (0.036 g, 0.296 mmol), cesium carbonate (0.080 g, 0.247 mmol), palladium (II) acetate (2.77 mg, 0.012 mmol), and Xantphos (10.71 mg, 0.019 mmol) in dioxane (2.4 mL) was heated in a Biotage Initiator microwave reactor at 170° C. for 10 min. The solids were filtered and the filtrate concentrated. The residue was suspended in dioxane (2 mL), treated with 20% sodium hydroxide (0.2 mL) and heated at 50° C. for 2 h. After cooling, the mixture was concentrated and the residue treated with water, sonicated, filtered, and purified by reversed-phase HPLC (Zorbax RX-C18 column (250×21.2 mm, 7 μm particle size) using a gradient of 10% to 100% acetonitrile: 0.1% aqueous trifluoroacetic acid over 40 min at a flow rate of 15 mL/minute) to give 9.0 mg of the title compound as the trifluoroacetate salt. $^1$H NMR (500 MHz, DMSO-D$_6$) 7.62 (dd, J=7.9, 4.88 Hz, 1H), 8.11 (s, 1H), 8.38 (d, J=2.8 Hz, 1H), 8.42-8.47 (m, 1H), 8.59 (d, J=2.8 Hz, 1H), 8.77 (d, J=3.1 Hz, 1H), 8.79 (dd, J=4.9, 1.5 Hz, 1H), 9.11 (s, 1H), 9.19 (d, J=2.1 Hz, 1H), 11.29 (s, 1H), 12.75 (s, 1H). MS (ESI) m/z 351.5 (M+H)$^+$.

Example 16

N-(6-chloro-4-(5H-pyrrolo[2,3-b]pyrazin-7-yl)pyridin-2-yl)piperidine-4-carboxamide A mixture of EXAMPLE 14A (0.050 g, 0.123 mmol), tert-butyl 4-carbamoylpiperidine-1-carboxylate (0.034 g, 0.148 mmol), cesium carbonate (0.040 g, 0.123 mmol), palladium (II) acetate (1.385 mg, 6.17 μmol), and Xantphos (5.35 mg, 9.25 μmol) in dioxane (1.2 mL) and N,N-dimethylformamide (0.1 mL) was heated in a Biotage Initiator microwave reactor at 170° C. for 10 min. The solids were filtered and the filtrate concentrated and purified by flash chromatography on silica gel eluted with a gradient of 90:10 to 85:15 dichloromethane/ethyl acetate. This intermediate was suspended in dioxane (1.5 mL) and treated with 20% sodium hydroxide (0.1 mL). The mixture was heated at 50° C. for 2 h. After concentration, the residue was triturated with water and filtered. The solids were dissolved in 1.5 mL of dichloromethane and trifluoroacetic acid (50 μM) and the mixture was stirred at ambient temperature for 60 min. After concentration, the residue was purified by reversed-phase HPLC (Zorbax RX-C18 column (250×21.2 mm, 7 μm particle size) using a gradient of 10% to 100% acetonitrile: 0.1% aqueous trifluoroacetic acid over 40 min at a flow rate of 15 mL/minute) to give 8.1 mg of the title compound as the trifluoroacetate salt. $^1$H NMR (400 MHz, CD$_3$OD) 1.96-2.07 (m, 2H), 2.09-2.20 (m, 2H), 2.76-2.87 (m, 1H), 3.02-3.14 (m, 2H), 3.44-3.55 (m, 2H), 8.07 (d, J=1.2 Hz, 1H), 8.32 (d, J=2.4 Hz, 1H), 8.40 (s, 1H), 8.55 (d, J=2.8 Hz, 1H), 8.82 (s, 1H). MS (ESI) m/z 357.4 (M+H)$^+$.

Example 17

N-(6-chloro-4-(5H-pyrrolo[2,3-b]pyrazin-7-yl)pyridin-2-yl)benzamide

Example 17A

N-(6-chloro-4-(5-(phenylsulfonyl)-5H-pyrrolo[2,3-b]pyrazin-7-yl)pyridin-2-yl)benzamide A mixture of EXAMPLE 14A (290.0 mg, 0.716 mmol), benzamide (95 mg, 0.787 mmol), cesium carbonate (233 mg, 0.716 mmol), palladium (II) acetate (8.03 mg, 0.036 mmol), and Xantphos (31.1 mg, 0.054 mmol) in dioxane (7 mL) and N,N-dimethylformamide (0.6 mL) was heated in a Biotage Initiator microwave reactor at 170° C. for 10 min. The solids were filtered and the filtrate concentrated and purified by flash chromatography eluted with a gradient of 97:5:2.5 to 95:5 dichloromethane/ethyl acetate to give 113 mg (32%) of the title compound.

Example 17B

N-(6-chloro-4-(5H-pyrrolo[2,3-b]pyrazin-7-yl)pyridin-2-yl)benzamide

A mixture of EXAMPLE 17A (40.0 mg, 0.082 mmol) and 20% sodium hydroxide (0.1 mL) in dioxane (1.5 mL) was heated at 50° C. for 2 h. The mixture was concentrated and the residue treated with water, sonicated, filtered, and washed with water. The solids were dissolved in 6 mL hot 1:1 dimethylsulfoxide/methanol. After cooling, a precipitate formed and additional methanol was added. The solids were filtered, washed with methanol, and dried to give 14.0 mg (32%) of the title compound. $^1$H NMR (300 MHz, DMSO-D$_6$) 7.41-7.67 (m, 3H), 7.95-8.16 (m, 3H), 8.39 (d, J=2.4 Hz, 1H), 8.60 (d, J=2.8 Hz, 1H), 8.77 (s, 1H), 9.08 (d, J=1.2 Hz, 1H), 10.98 (s, 1H), 12.74 (s, 1H). MS (ESI) m/z 350.5 (M+H)$^+$.

Example 18

6-chloro-4-(5H-pyrrolo[2,3-b]pyrazin-7-yl)pyridin-2-amine

A mixture of EXAMPLE 17A (0.130 g, 0.265 mmol) and concentrated hydrochloric acid (0.15 mL) in ethanol (6 mL) was heated at 95° C. for 24 h. The mixture was concentrated and the residue treated with saturated aqueous sodium bicarbonate, sonicated, filtered, and washed with water. The intermediate was suspended in dioxane (3.5 mL), treated with 20% sodium hydroxide (0.3 mL) and heated at 50° C. for 2 h. After concentration, the residue was treated with 6 mL of water. The solid was filtered, washed with water, and purified by reversed-phase HPLC (Zorbax RX-C18 column (250× 21.2 mm, 7 μm particle size) using a gradient of 10% to 100% acetonitrile: 0.1% aqueous trifluoroacetic acid over 40 min at a flow rate of 15 mL/minute). The filtrate was also separately purified by HPLC to obtain a combined 46.5 mg (49%) of the title compound as the trifluoroacetate salt. $^1$H NMR (500 MHz, DMSO-d$_6$) 7.28 (s, 1H), 7.47 (s, 1H), 8.34 (d, J=2.4 Hz, 1H), 8.52 (d, J=2.8 Hz, 1H), 8.58 (d, J=3.1 Hz, 1H), 12.55 (s, 1H). MS (ESI) m/z 246.3 (M+H)+.

Example 19

N¹-(6-chloro-4-(5H-pyrrolo[2,3-b]pyrazin-7-yl)pyridin-2-yl)-2,2-dimethylpropane-1,3-diamine

Example 19A 7-(2,6-dichloropyridin-4-yl)-5H-pyrrolo[2,3-b]pyrazine

A suspension of EXAMPLE 14A (0.300 g, 0.740 mmol) in ethanol (6 mL) was treated with a solution of potassium hydroxide (0.166 g, 2.96 mmol) in water (1.5 mL). The mixture was heated at 50° C. for 1.5 h. After cooling, the mixture was concentrated and 20% brine, sodium bicarbonate, and ethyl acetate were added. The suspension in both layers was filtered, washed with water, and dried to give the title compound. The organic layer in the filtrate was separated, dried, and concentrated. The residue was treated with ethyl acetate and diethyl ether, filtered, washed with diethyl ether, and dried to give additional title compound for a combined yield of 0.140 g (71%).

Example 19B

N¹-(6-chloro-4-(5H-pyrrolo[2,3-b]pyrazin-7-yl)pyridin-2-yl)-2,2-dimethylpropane-1,3-diamine A mixture of EXAMPLE 19A (90.0 mg, 0.339 mmol) in 2,2-dimethylpropane-1,3-diamine (1.6 mL) was heated in a Biotage Initiator microwave reactor at 160° C. for 25 min. The solution was diluted with 20% brine and washed with ethyl acetate. The organic layer was washed with 20% brine, dried and concentrated. The residue was triturated with 1:1 ethyl acetate/diethyl ether. The solid was filtered, washed with diethyl ether and dried. The filtrate was concentrated, triturated with ethyl acetate and diethyl ether, and filtered. The combined solids were purified by reversed-phase HPLC (Zorbax RX-C18 column (250×21.2 mm, 7 μm particle size) using a gradient of 10% to 100% acetonitrile: 0.1% aqueous trifluoroacetic acid over 40 min at a flow rate of 15 mL/minute). The trifluoroacetate salt obtained was dissolved in methanol and treated with 1M hydrogen chloride in diethyl ether. The precipitate was filtered, washed with diethyl ether, and dried to give 35.5 mg (26%) of the title compound as the hydrochloride salt. ¹H NMR (500 MHz, DMSO-d₆) 1.00 (s, 6 H), 2.70 (d, J=5.8 Hz, 2H), 3.22 (s, 2H), 7.30 (s, 1H, brd), 7.33 (s, 1H), 7.63 (s, 2H, brd), 8.01 (s, 1H), 8.36 (d, J=2.4 Hz, 1H), 8.54 (d, J=2.4 Hz, 1H), 8.64 (d, J=3.1 Hz, 1H), 12.65 (s, 1H). MS (ESI) m/z 331.3 (M+H)+.

Example 20

N-(trans 4-(6-chloro-4-(5H-pyrrolo[3,2-b]pyrazin-7-yl)pyridin-2-ylamino)cyclohexyl)-5-oxopyrrolidine-2-carboxamide To a solution of 5-oxopyrrolidine-2-carboxylic acid (0.047 g, 0.368 mmol), EDC (0.1 g, 0.525 mmol), HOBT (0.08 g, 0.525 mmol) and diisopropylethylamine (0.136 g, 1.05 mmol) in 3 mL N,N-dimethylformamide was added EXAMPLE 7B (0.12 g, 0.35 mmol). The solution was stirred at ambient temperature for 3 h and diluted with ethyl acetate. The organic layer was washed with water and brine, dried over magnesium sulfate, filtered, and concentrated. Flash chromatography on silica gel eluting with a gradient of 0 to 10% methanol in dichloromethane provided 6 mg of the title compound as an off-white solid. ¹H NMR (300 MHz, DMSO-D6) δ 1.25-1.39 (m, 4H) 1.75-2.03 (m, 4H) 2.04-2.30 (m, 4H) 3.47-3.69 (m, 2H) 3.95 (d, 1H) 6.87 (d, J=7.80 Hz, 1H) 7.24 (s, 1H) 7.45 (s, 1H) 7.76 (s, 1H) 7.84 (d, J=7.80 Hz, 1H) 8.34 (d, J=2.71 Hz, 1H) 8.51 (d, J=2.71 Hz, 1H) 8.57 (s, 1H) 12.37-12.65 (m, 1H); MS (ESI) m/z 454.7 (M+H)+

Example 21

4-chloro-N-cyclohexyl-6-(5H-pyrrolo[3,2-b]pyrazin-7-yl)pyrimidin-2-amine

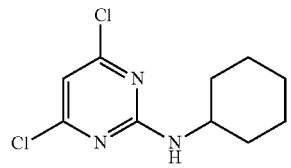 [SMILES: Clc1cc(Cl)nc(NC2CCCCC2)n1]

Example 21A 4,6-dichloro-N-cyclohexylpyrimidin-2-amine

To a solution of cyclohexanamine (1.1 mL, 9.57 mmol) in ethyl acetate (10 mL) was added 2,4,6-trichloropyrimidine (1.0 mL, 8.70 mmol) dropwise at 0° C. followed by dropwise addition of diisopropylethylamine (1.8 mL, 10.4 mmol). The reaction was warmed to ambient temperature and stirred for 3 h. Additional cyclohexanamine (0.3 mL) and diisopropylethylamine (0.5 mL) were added. After 4 h, the mixture was diluted with ethyl acetate and washed with 20% brine. The organic layer was dried over magnesium sulfate, filtered, and concentrated. The resulting oil was purified by flash chromatography on silica gel eluting with a gradient of 92:8 to 85:15 hexane/ethyl acetate to give 0.740 g (35%) of the title compound.

Example 21B 4-chloro-N-cyclohexyl-6-(5H-pyrrolo[3,2-b]pyrazin-7-yl)pyrimidin-2-amine A mixture of Example 2B (80.0 mg, 0.190 mmol), Example 21A (140.0 mg, 0.569 mmol), bis(tri-t-butylphosphine)palladium(0) (9.7 mg, 0.019 mmol) and cesium fluoride (14.4 mg, 0.095 mmol) was purged with nitrogen and anhydrous dioxane (2 mL) added. The mixture was purged with nitrogen and heated at 70° C. for 3 h. 20% Sodium hydroxide solution (0.1 mL) was added and the mixture stirred at 80° C. for 30 min. The mixture was concentrated and purified by reverse phase HPLC to afford the title compound (10 mg, 16% yield). MS (ESI) m/e 329 (M+H)+; ¹H NMR (400 MHz, DMSO-D6) 1.13-1.45 (m, 5H) 1.56-1.66 (m, 1H) 1.69-1.81 (m, 2H) 1.88-1.99 (m, 2H) 3.83 (s, 1H) 6.87 (s, 1H) 7.77 (s, 1H) 8.34 (d, J=2.44 Hz, 1H) 8.48 (d, J=2.75 Hz, 1H) 8.54 (d, J=2.75 Hz, 1H) 12.42 (s, 1H).

Example 22

N-(trans 4-((6-chloro-4-(5H-pyrrolo[2,3-b]pyrazin-7-yl)pyridin-2-yl)(ethyl)amino)cyclohexyl)cyclopropanecarboxamide The title compound was produced as a side product in the procedure described in EXAMPLE 8. Yield: 15 mg (36%). MS (DCI/NH$_3$) m/z 439 (M+H)$^+$; $^1$H NMR (300 MHz, DMSO-d$_6$): 0.58-0.68 (m, 4H), 1.20-1.36 (m, 4H), 1.47 (t, J=7.29 Hz, 3H), 1.45-1.60 (m, 1H), 1.82 (s, 2H), 1.89-2.09 (m, 2H), 3.40-3.83 (m, 2H), 4.35 (q, J=7.35 Hz, 2H), 6.90 (d, J=7.80 Hz, 1H), 7.19 (s, 1H), 7.43 (s, 1H), 7.95 (d, J=7.80 Hz, 1H), 8.38 (s, 1H), 8.56 (s, 1H), 8.70 (s, 1H).

Example 23

N-(3-(6-chloro-4-(5H-pyrrolo[2,3-b]pyrazin-7-yl)pyridin-2-ylamino)cyclohexyl)-2-(dimethylamino)acetamide

Example 23A

N-(3-(6-chloro-4-iodopyridin-2-ylamino)cyclohexyl)-2-(dimethylamino)acetamide

The title compound was prepared according to the procedure for EXAMPLE 5, substituting EXAMPLE 11A for EXAMPLE 3 and 2-(dimethylamino)acetic acid for cyclopropanecarboxylic acid. The crude product was purified by flash chromatography on silica gel eluting with ethyl acetate to provide 80 mg of the title compound. Yield: 64%. MS (DCI/NH$_3$) m/z 437 (M+H)$^+$.

Example 23B

N-(3-(6-chloro-4-(5H-pyrrolo[2,3-b]pyrazin-7-yl)pyridin-2-ylamino)cyclohexyl)-2-(dimethylamino)acetamide The title compound was prepared according to procedure for EXAMPLE 6C, substituting EXAMPLE 23A for EXAMPLE 6B. The material was purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt. Yield: 6 mg (8%). MS (DCI/NH$_3$) m/z 428 (M+H)$^+$; $^1$H NMR (300 MHz, DMSO-D6): 0.99-1.28 (m, 2H), 1.29-1.52 (m, 1H), 1.54-1.98 (m, 4H), 2.13 (d, J=11.50 Hz, 1H), 2.79 (s, 6H), 3.68-4.15 (m, 4H), 7.25 (s, 1H), 7.48 (s, 1H), 8.35 (d, J=2.38 Hz, 1H), 8.49 (d, J=7.53 Hz, 1H), 8.52 (d, J=2.38 Hz, 1H), 8.60 (d, J=3.17 Hz, 1H), 9.62 (s, 1H), 12.55 (s, 1H).

Example 24

N-(3-((6-chloro-4-(5H-pyrrolo[2,3-b]pyrazin-7-yl)pyridin-2-yl)(ethyl)amino)cyclohexyl)-2-(dimethylamino)acetamide The trifluoroacetate salt of the title compound was produced as a side product in the synthesis of EXAMPLE 23. Yield: 8 mg (10%). MS (DCI/NH$_3$) m/z 456 (M+H)$^+$; $^1$H NMR (300 MHz, DMSO-d$_6$): 0.98-1.29 (m, 2H), 1.31-1.44 (m, 1H), 1.46 (t, J=7.23 Hz, 3H), 1.59-1.97 (m, 4H), 2.13 (d, J=14.58 Hz, 1H), 2.79 (s, 6H), 3.52-4.13 (m, 4H), 4.35 (q, J=7.23 Hz, 2H), 7.20 (s, 1H), 7.45 (s, 1H), 8.39 (d, J=2.37 Hz, 1H), 8.48 (d, J=7.80 Hz, 1H), 8.56 (d, J=2.37 Hz, 1H), 8.72 (s, 1H), 9.62 (s, 1H).

Example 25

N-(3-(6-chloro-4-(5H-pyrrolo[2,3-b]pyrazin-7-yl)pyridin-2-ylamino)cyclohexyl)furan-2-sulfonamide

Example 25A

N-(3-(6-chloro-4-iodopyridin-2-ylamino)cyclohexyl)furan-2-sulfonamide

The title compound was prepared according to procedure for EXAMPLE 13A, substituting furan-2-sulfonyl chloride for methanesulfonyl chloride. Yield: 20 mg (20%). MS (DCI/NH$_3$) m/z 421 (M+H)$^+$.

Example 25B

N-(3-(6-chloro-4-(5H-pyrrolo[2,3-b]pyrazin-7-yl)pyridin-2-ylamino)cyclohexyl)furan-2-sulfonamide The title compound was prepared according to procedure for EXAMPLE 6C, substituting EXAMPLE 25A for EXAMPLE 6B. The material was purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt. Yield: 20 mg (20%). MS (DCI/NH$_3$) m/z 421 (M+H)$^+$; $^1$H NMR (300 MHz, DMSO-d$_6$): 0.95-1.27 (m, 4H), 1.47-1.73 (m, 2H), 1.73-1.86 (m, 1H), 1.87-2.01 (m, 1H), 3.01-3.27 (m, 1H), 3.94-4.13 (m, 1H), 6.60 (dd, J=3.56, 1.86 Hz, 1H), 6.90 (s, 1H), 7.06 (d, J=3.39 Hz, 1H), 7.26 (s, 1H), 7.40 (s, 1H), 7.83-7.93 (m, 1H), 8.09 (d, J=8.14 Hz, 1H), 8.34 (d, J=2.71 Hz, 1H), 8.52 (d, J=2.71 Hz, 1H), 8.58 (d, J=3.05 Hz, 1H), 12.54 (s, 1H).

Example 26

Enzyme Inhibition Data

This example describes the assays that may be used to identify compounds having kinase activity.

Cdc7 (BEV coexpressed huCDC7/DBF$_4$) is prepared internally. Cdc7 assays are conducted as follows with final concentrations as listed. In 384-well v-bottom polypropylene plates, 6 L compound (2% DMSO), is mixed with 6 L of Cdc7 (2 µg/mL), and Jerini peptide substrate A-All (biotin-C$_6$linker-TPSDSLIYDDGLS) (2 µM), followed by immediate initiation with 6 L λ-[$^{33}$P]-ATP (1 µM, 20 mCi/µmol) using a reaction buffer comprising 25 mM HEPES, pH 7.5, 1 mM DTT, 10 mM MgCl$_2$, 100 µM Na$_3$VO$_4$, 0.075 mg/ml Triton X-100. Reactions are quenched after 1 hr by the addition of 90 L stop buffer (50 mM EDTA, 2M NaCl). 85 µL of the stopped reactions are transferred to 384-well streptavidin-coated plates (FlashPlate Plus, Perkin Elmer), incubated 30 minutes at room temperature and washed 3 times with 0.05% Tween-20/PBS using an ELX-405 automated plate washer (BioTek), and counted on a TopCount Scintillation Plate Reader (Packard). IC50 values are determined via non-linear regression fitting of enzyme inhibition data and corresponding Ki values are generated assuming ATP-competitive (equilibrium) inhibition and using the experimentally determined apparent ATP Km of 0.7 µM (as determined using the above assay condition, but varying ATP). Table 1 depicts enzyme inhibition data (K$_i$) for exemplary compounds. In Table 1, "A" represents a K$_i$ of less than 10 nM, "B" represents a K$_i$ of between 10 nM and 100 nM, and "C" represents a K$_i$ of greater than 100 nM.

TABLE 1

| Example | Cdc7 Inhibition |
|---------|-----------------|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | B |
| 18 | A |
| 19 | A |
| 20 | A |
| 21 | C |
| 22 | C |
| 23 | A |
| 24 | C |
| 25 | A |

Compounds of the present invention assessed by the above-described assays were found to have Cdc7 kinase-inhibiting activity.

Example 27

6-chloro-N-(1-methylpiperidin-3-yl)-4-(5H-pyrrolo[2,3-b]pyrazin-7-yl)pyridin-2-amine Example 27A 6-chloro-4-iodo-N-(piperidin-3-yl)pyridin-2-amine A mixture of 2,6-dichloro-4-iodopyridine (1 g, 3.65 mmol) and tert-butyl 3-aminopiperidine-1-carboxylate (3.66 g, 18 mmol) in a sealed tube was heated at 120° C. for three days. The reaction mixture was poured into water. The solid was collected by filtration. The crude product was dissolved in CH$_2$Cl$_2$. To the solution was added TFA (2 mL). The mixture was stirred at room temperature for 3 hours. The reaction was concentrated and the residue was purified by HPLC (Zorbax, C-18, 250×2.54 column, Mobile phase A: 0.1% trifluoroacetic acid in water; B: 0.1% trifluoroacetic acid in acetonitrile; 0-100% gradient) to give the TFA salt of the title compound. Yield: 500 mg (33%). MS (DCI/NH$_3$) m/z 338 (M+H)$^+$.

Example 27B 6-chloro-4-iodo-N-(1-methylpiperidin-3-yl)pyridin-2-amine

To a mixture of EXAMPLE 27A (51 mg, 0.15 mmol) in methanol (5 mL) was added formaldehyde (10 mg, 0.3 mmol). The solution was stirred at room temperature for 10 minutes before NaBH$_3$CN (18 mg, 0.29 mmol) and ZnCl (catalytic amount) were added. The reaction mixture was stirred overnight at room temperature. The solvent was removed and the residue was purified by HPLC. (Zorbax, C-18, 250×2.54 column, Mobile phase A: 0.1% trifluoroacetic acid in water; B: 0.1% trifluoroacetic acid in acetonitrile; 0-100% gradient) to provide the TFA salt of the title compound (yield: 44 mg, 84%). MS (DCI/NH$_3$) m/z 352 (M+H)$^+$.

Example 27C 6-chloro-N-(1-methylpiperidin-3-yl)-4-(5-(phenylsulfonyl)-5H-pyrrolo[3,2-b]pyrazin-7-yl)pyridin-2-amine A round bottom flask was charged with EXAMPLE 27B (70 mg, 0.20 mmol), EXAMPLE 2B (92 mg, 0.22 mmol), bis(tri-tert-butylphosphine)palladium(0) (10 mg, 0.02 mmol) and CsF (30 mg, 0.22 mmol), and the mixture was purged with nitrogen. Anhydrous dioxane (10 mL) was added via syringe. The solution was purged with nitrogen again and heated at 90° C. for 4 hours. The reaction mixture was partitioned between EtOAc and brine and the organic phase was concentrated. The residue was purified by flash chromatography (eluted with EtOAc/hexane: 1:2) to give the title compound. Yield: 50 mg (52%). MS (DCI/NH$_3$) m/z 483 (M+H)$^+$.

Example 27D 6-chloro-N-(1-methylpiperidin-3-yl)-4-(5H-pyrrolo[3,2-b]pyrazin-7-yl)pyridin-2-amine To a solution of EXAMPLE 27C (50 mg, 0.1 mmol) in dioxane (5 mL) was added NaOH powder (100 mg, 2.5 mmol). The mixture was stirred at 50° for 17 hours. The reaction mixture was concentrated and purified by HPLC (Zorbax, C-18, 250×2.54 column, Mobile phase A: 0.1% trifluoroacetic acid in water; B: 0.1% trifluoroacetic acid in acetonitrile; 0-100% gradient) to give the TFA salt of the title compound. Yield: 33 mg (93%). MS (DCI/NH$_3$) m/z 343 (M+H)$^+$, $^1$H NMR (300 MHz, DMSO-d$_6$): 1.35-1.52 (m, 1 H), 1.64-1.87 (m, 2H), 1.88-2.05 (m, 2H), 2.70-2.75 (m, 1H), 2.76-2.82 (m, 1H), 2.84 (s, 3H), 3.51-3.66 (m, 1H), 4.05-4.23 (m, 1H), 7.26 (d, J=7.80 Hz, 1H), 7.33 (s, 1H), 7.60 (s, 1H), 8.36 (d, J=2.71 Hz, 1H), 8.53 (d, J=2.37 Hz, 1H), 8.62 (d, J=3.05 Hz, 1H), 12.60 (s, 1H).

Example 28

6-chloro-N-[(1-methylpiperidin-3-yl)methyl]-4-(5H-pyrrolo[2,3-b]pyrazin-7-yl)pyridin-2-amine Example 28A 6-chloro-4-iodo-N-(piperidin-3-ylmethyl)pyridin-2-amine The TFA salt of the title compound was prepared according to the procedure for EXAMPLE 27A substituting benzyl 3-(aminomethyl)piperidine-1-carboxylate for tert-butyl 3-aminopiperidine-1-carboxylate. Yield: 1.2 g (45%). MS (DCI/NH$_3$) m/z 352 (M+H)$^+$.

Example 28B 6-chloro-4-iodo-N-((1-methylpiperidin-3-yl)methyl)pyridin-2-amine

The TFA salt of the title compound was prepared according to the procedure for EXAMPLE 27B substituting EXAMPLE 28A for EXAMPLE 27A. Yield: 180 mg (87%). MS (DCI/NH$_3$) m/z 366 (M+H)$^+$.

Example 28C 6-chloro-N-((1-methylpiperidin-3-yl)methyl)-4-(5-(phenylsulfonyl)-5H-pyrrolo[3,2-b]pyrazin-7-yl)pyridin-2-amine The title compound was prepared according to the procedure for EXAMPLE 27C substituting EXAMPLE 28B for EXAMPLE 27B. Yield: 50 mg (27%). MS (DCI/NH$_3$) m/z 497 (M+H)$^+$.

Example 28D 6-chloro-N-((1-methylpiperidin-3-yl)methyl)-4-(5H-pyrrolo[3,2-b]pyrazin-7-yl)pyridin-2-amine The TFA salt of the title compound was prepared according to the procedure for EXAMPLE 27D substituting EXAMPLE 28C for EXAMPLE 27C. Yield: 10 mg (47%). MS (DCI/NH$_3$) m/z 357 (M+H)$^+$, $^1$H NMR (300 MHz, DMSO-d$_6$): 0.98-1.41 (m, 2H), 1.46-1.73 (m, 1H), 1.74-1.97 (m, 2H), 1.98-2.21 (m, 1H), 2.61-2.76 (m, 2H), 2.78 (d, J=4.75 Hz, 3H), 3.06-3.51 (m, 3H), 7.18 (s, 1H), 7.29 (s, 1H), 7.55 (s, 1H), 8.36 (d, J=2.71 Hz, 1H), 8.53 (d, J=2.71 Hz, 1H), 8.62 (d, J=3.05 Hz, 1H), 12.57 (d, J=2.71 Hz, 1H).

Example 29

N-(trans-4-{[6-chloro-4-(5H-pyrrolo[2,3-b]pyrazin-7-yl)pyridin-2-yl]amino}cyclohexyl)-1-ethylpyrrolidine-3-carboxamide The title compound (0.05 g) was prepared according to the procedure for EXAMPLE 20, substituting 1-ethylpyrrolidine-3-carboxylic acid for 5-oxopyrrolidine-2-carboxylic acid. $^1$H NMR (300 MHz, DMSO-d$_6$) ppm 1.00 (q, J=6.67 Hz, 3H) 1.21-1.40 (m, 4H) 1.67-1.95 (m, 5H) 2.22-2.46 (m, 5H) 2.55-2.72 (m, 1H) 2.72-2.86 (m, 2H) 3.56 (m, 2H) 6.87 (d, J=7.80 Hz, 1H) 7.23 (s, 1H) 7.45 (s, 1H) 7.69 (d, J=7.80 Hz, 1H) 8.34 (d, J=2.71 Hz, 1H) 8.52 (d, J=2.37 Hz, 1H) 8.58 (s, 1H) 12.53 (s, 1H). MS (ESI) m/z 468.3 (M+H)$^+$.

Example 30

(2S)—N-(trans-4-{[6-chloro-4-(5H-pyrrolo[2,3-b]pyrazin-7-yl)pyridin-2-yl]amino}cyclohexyl)azetidine-2-carboxamide The title compound (0.055 g) was prepared according to the procedure for EXAMPLE 20, substituting 1-(tert-butoxycarbonyl)azetidine-2-carboxylic acid for 5-oxopyrrolidine-2-carboxylic acid. The BOC group from the intermediate was removed with treatment of the intermediate with a 2M HCl in ether solution, followed by filtration of the white solid to give the title compound as the HCl salt. $^1$H NMR (300 MHz, DMSO-d$_6$) ppm 1.33 (s, 4H) 1.74-2.08 (m, 4H) 2.22-2.44 (m, 2H) 2.54-2.75 (m, 2H) 3.56-3.70 (m, 1H) 3.69-3.85 (m, 1H) 3.84-4.05 (m, 1H) 4.82 (d, J=7.80 Hz, 1H) 6.88 (d, J=2.03 Hz, 1H) 7.17-7.31 (m, 1 H) 7.47 (s, 1H) 8.26-8.41 (m, 2H) 8.52 (d, J=2.71 Hz, 1H) 8.58 (d, J=3.05 Hz, 1H) 8.72 (s, 1H) 9.11 (s, 1H) 12.54 (s, 1H). MS (ESI) m/z 426.2 (M+H)$^+$.

Example 31

N-(trans-4-{[6-chloro-4-(5H-pyrrolo[2,3-b]pyrazin-7-yl)pyridin-2-yl]amino}cyclohexyl)-2,6-dioxopiperidine-4-carboxamide The title compound (0.05 g) was prepared according to the procedure for EXAMPLE 20, substituting 2,6-dioxopiperidine-4-carboxylic acid for 5-oxopyrrolidine-2-carboxylic acid. $^1$H NMR (300 MHz, DMSO-d$_6$) ppm 1.28 (t, J=9.49 Hz, 5H) 1.80 (s, 2H) 1.98 (d, J=3.73 Hz, 2H) 2.52-2.62 (m, 3H) 2.82-2.98 (m, 1H) 3.38-3.70 (m, 2H) 6.87 (d, J=8.14 Hz, 1H) 7.24 (s, 1H) 7.45 (s, 1H) 7.94 (d, J=7.80 Hz, 1H) 8.34 (d, J=2.37 Hz, 1H) 8.46-8.55 (m, 1H) 8.54-8.63 (m, 1H) 10.63 (s, 1H) 12.53 (s, 1H). MS (ESI) m/z 482.4 (M+H)$^+$.

Example 32

N-(trans-4-{[6-chloro-4-(5H-pyrrolo[2,3-b]pyrazin-7-yl)pyridin-2-yl]amino}cyclohexyl)-N$^2$,N$^2$-dimethylalaninamide The title compound (0.06 g) was prepared according to the procedure for EXAMPLE 20, substituting 2-(dimethylamino)propanoic acid for 5-oxopyrrolidine-2-carboxylic acid. $^1$H NMR (300 MHz, DMSO-d$_6$) ppm 1.08 (d, J=6.78 Hz, 3H) 1.15-1.50 (m, 4H) 1.78 (d, J=3.73 Hz, 2H) 1.89-2.05 (m, 2H) 2.19 (s, 6H) 2.79-3.04 (m, 1H) 3.42-3.75 (m, 2H) 6.87 (d, J=7.80 Hz, 1H) 7.23 (s, 1H) 7.45 (s, 1H) 7.57 (d, J=8.14 Hz, 1H) 8.34 (d, J=2.37 Hz, 1H) 8.52 (d, J=2.71 Hz, 1H) 8.57 (d, J=2.71 Hz, 1H) 12.52 (s, 1H). MS (ESI) m/z 442.4 (M+H)$^+$.

Example 33 trans 4-{[6-chloro-4-(2-chloro-5H-pyrrolo[2,3-b]pyrazin-7-yl)pyridin-2-yl]amino}cyclohexanol

Example 33A 2-chloro-7-iodo-5H-pyrrolo[2,3-b]pyrazine

A 1 M solution of iodine monochloride in dichloromethane (9.84 mL, 9.84 mmol) was added dropwise to an ice-cold solution of 2-chloro-5H-pyrrolo[2,3-b]pyrazine (6.75 g, 11.07 mmol) in anhydrous pyridine (12 mL). The reaction mixture was stirred at 0° C. for 60 minutes, then concentrated. The residue was partitioned between ethyl acetate and brine. The organic phase was washed with brine and concentrated. The crude product was stirred with 15 mL of dichloromethane. The yellow solid material was collected by filtration, washed with dichloromethane and dried to give 2.86 g of the title product. Yield: 66%. MS (DCI$^+$) m/z 280 (M+H)$^+$.

Example 33B 2-chloro-7-iodo-5-(phenylsulfonyl)-5H-pyrrolo[2,3-b]pyrazine

Sodium hydride (60% in mineral oil, 404 mg, 10.09 mmol) was added to an ice-cold solution of EXAMPLE 33A (2.35 g, 8.41 mmol) in anhydrous DMF (20 mL) under nitrogen. The reaction mixture was stirred at 0° C. for 30 minutes and benzenesulfonyl chloride (1.19 mL, 9.25 mmol) was then added. The ice-bath was removed and the mixture was stirred at room temperature overnight. This reaction was quenched with the addition of 50 mL of water. An off white solid material was collected by filtration, washed with water and hexane, and dried to give 3.38 g of the title product. Yield: 96%. MS (DCI$^+$) m/z 280 (M+H)$^+$.

Example 33C trans 4-(6-chloro-4-(4,4,5,5-tetramethyl-1,3,2-dioxaborolan-2-yl)pyridin-2-ylamino)cyclohexanol The title compound was prepared according to the same protocol as EXAMPLE 1B, substituting EXAMPLE 2A for EXAMPLE 1A. MS (DCI/NH$_3$) m/z 353 (M+H)$^+$.

Example 33D trans 4-(6-chloro-4-(2-chloro-5-(phenylsulfonyl)-5H-pyrrolo[3,2-b]pyrazin-7-yl)pyridin-2-ylamino)cyclohexanol A 50 mL round bottom flask was charged with EXAMPLE 33B (108 mg, 0.258 mmol), EXAMPLE 33C (100 mg, 0.284 mmol), and PdCl$_2$(dppf)-CH$_2$Cl$_2$ adduct (14.8 mg, 0.018 mmol), and was purged with nitrogen. DMF (6 mL) and sodium bicarbonate (217 mg, 2.58 mmol) in 1.5 mL of water were then added. This mixture was purged with nitrogen again, and was heated at 65° C. for 30 minutes. After cooling, the reaction mixture was partitioned between ethyl acetate and brine. The organic phase was washed with brine and concentrated. The residue was separated by flash chromatography (eluted with 10-40% gradient EtOAc in hexane) to give the title product. Yield: 88 mg (66%). MS (DCI/NH$_3$) m/z 518 (M+H)$^+$.

Example 33E

4-{[6-chloro-4-(2-chloro-5H-pyrrolo[2,3-b]pyrazin-7-yl)pyridin-2-yl]amino}cyclohexanol To a suspension of EXAMPLE 33D (40 mg, 0.077 mmol) in dioxane (4 mL) was added a 50% NaOH solution in water (100 mg, 1.25 mmol). This solution was heated at 90° C. for 2 hours, and concentrated. The residual solid was stirred with 4 mL of water, filtered, washed with water, 1 mL of dioxane, and dried to give the title product. Yield: 29 mg (99%). MS (DCI/NH$_3$) m/z 518 (M+H)$^+$; $^1$H NMR (400 MHz, DMSO-d$_6$): 1.24-1.31 (m, 4H), 1.82-1.89 (m, 2H), 1.92-1.97 (m, 2H), 3.57 (s, 2H), 4.55 (d, J=4.27 Hz, 1H), 6.90 (d, J=7.63 Hz, 1H), 7.14 (s, 1H), 7.29 (s, 1H), 8.42 (s, 1H), 8.68 (s, 1H), 12.92 (br s, 1H).

Example 34 trans 4-{[4-(2-bromo-5H-pyrrolo[2,3-b]pyrazin-7-yl)-6-chloropyridin-2-yl]amino}cyclohexanol The title product was prepared according to the same protocol as EXAMPLE 33, substituting 2-bromo-5H-pyrrolo[2,3-b]pyrazine for 2-chloro-5H-pyrrolo[2,3-b]pyrazine in EXAMPLE 33A. MS (DCI/NH$_3$) m/z 422, 424 (M+H)$^+$; $^1$H NMR (500 MHz, DMSO-d$_6$): 1.22-1.30 (m, 4H), 1.84-1.88 (m, 2H), 1.92-1.96 (m, 2H), 3.35-3.42 (m, 2H), 3.53-3.59 (m, 1H), 6.95 (br s, 1H), 7.14 (s, 1H), 7.29 (s, 1H), 8.47 (s, 1H), 8.66 (d, J=3.05 Hz, 1H), 12.84 (d, J=2.44 Hz, 1H).

Example 35

6-chloro-4-(2-chloro-5H-pyrrolo[2,3-b]pyrazin-7-yl)-N-cyclohexylpyridin-2-amine

The title product was prepared according to the same protocol as EXAMPLE 33, substituting EXAMPLE 1B for EXAMPLE 33C used in EXAMPLE 33D. MS (DCI/NH$_3$) m/z 362 (M+H)$^+$; $^1$H NMR (400 MHz, DMSO-d$_6$): 1.14-1.26 (m, 2H), 1.29-1.39 (m, 2 H), 1.59-1.63 (m, 1H), 1.74 (dd, J=9.77, 3.36 Hz, 2H), 1.90-1.96 (m, 2H), 3.60-3.68 (m, 2H), 6.92 (d, J=7.63 Hz, 1H), 7.13 (s, 1H), 7.29 (s, 1H), 8.40 (s, 1H), 8.67 (s, 1H).

Example 36

7-[2-chloro-6-(cyclohexylamino)pyridin-4-yl]-5H-pyrrolo[2,3-b]pyrazine-2-carboxylic acid

Example 36A 6-chloro-N-cyclohexyl-4-(trimethylstannyl)pyridin-2-amine

The title compound was prepared according to the procedure for EXAMPLE 2B substituting 6-chloro-N-cyclohexyl-4-iodopyridin-2-amine for EXAMPLE 1C.

Example 36B 7-(2-chloro-6-(cyclohexylamino)pyridin-4-yl)-5H-pyrrolo[3,2-b]pyrazine-2-carboxylic acid A 50 mL round bottom flash was charged with methyl 7-iodo-5-(phenylsulfonyl)-5H-pyrrolo[2,3-b]pyrazine-2-carboxylate (100 mg, 0.23 mmol), EXAMPLE 36A(84 mg, 0.23 mmol), Pd$_2$(dba)$_3$ (21 mg, 0.022 mmol), tri(o-tolyl)phosphine (21 mg, 0.065 mmol), and triethylamine (0.09 mL, 0.646 mmol) in ahydrous DMF (8 mL). The mixture was purged with nitrogen, and heated at 80° C. for three days. The reaction mixture was partitioned between ethyl acetate and brine. The residue was purified by HPLC (Zorbax, C-18, 250×2.54 column, Mobile phase A: 0.1% trifluoroacetic acid in water; B: 0.1% trifluoroacetic acid in acetonitrile; 0-100% gradient) to give the TFA salt of the title compound. Yield: 18 mg (25%). MS (DCI/NH$_3$) m/z 372 (M+H)$^+$, $^1$H NMR (300 MHz, DMSO-d$_6$): 0.97-1.49 (m, 5 H), 1.61 (d, J=11.90 Hz, 1H), 1.73 (d, J=12.29 Hz, 2H), 1.94 (d, J=11.90 Hz, 2H), 3.48-3.68 (m, 1H), 7.28 (s, 1H), 7.44 (s, 1H), 8.73 (d, J=2.78 Hz, 1H), 8.97 (s, 1H), 12.89 (d, J=2.38 Hz, 1H).

Example 37

7-[2-chloro-6-(cyclohexylamino)pyridin-4-yl]-5H-pyrrolo[2,3-b]pyrazine-2-carbonitrile The TFA salt of the title compound was prepared according to the procedure for EXAMPLE 36, substituting 7-iodo-5-(phenylsulfonyl)-5H-pyrrolo[2,3-b]pyrazine-2-carbonitrile for methyl 7-iodo-5-(phenylsulfonyl)-5H-pyrrolo[2,3-b]pyrazine-2-carboxylate. Yield: 28 mg (35%). MS (DCI/NH$_3$) m/z 353 (M+H)$^+$, $^1$H NMR (300 MHz, DMSO-d$_6$): 1.08-1.46 (m, 5H), 1.54-1.67 (m, 1H), 1.68-1.81 (m, 2H), 1.93 (d, J=11.53 Hz, 2H), 3.51-3.74 (m, 1H), 6.99 (s, 1H), 7.14 (s, 1H), 7.38 (s, 1H), 8.87 (d, J=3.05 Hz, 1H), 8.90 (s, 1 H), 13.18 (s, 1H).

Example 38

6-chloro-N-cyclohexyl-4-(2-phenyl-5H-pyrrolo[2,3-b]pyrazin-7-yl)pyridin-2-amine

Example 38A 4-(2-bromo-5-(phenylsulfonyl)-5H-pyrrolo[3,2-b]pyrazin-7-yl)-6-chloro-N-cyclohexylpyridin-2-amine The title product was prepared according to the same protocol as EXAMPLE 33, substituting EXAMPLE 1B for EXAMPLE 33C used in EXAMPLE 33D, and substituting 2-bromo-5H-pyrrolo[2,3-b]pyrazine for 2-chloro-5H-pyrrolo[2,3-b]pyrazine used in EXAMPLE 33A. MS (DCI/NH$_3$) m/z 546, 548 (M+H)$^+$.

Example 38B 6-chloro-N-cyclohexyl-4-(2-phenyl-5H-pyrrolo[2,3-b]pyrazin-7-yl)pyridin-2-amine A mixture of EXAMPLE 38A (40 mg, 0.073 mmol), phenylboronic acid (11 mg, 0.088 mmol) and dichlorobis(triphenylphosphine)palladium (II) (5 mg, 0.007 mmol) was suspended in a mixture of 7:3:2 DME/H$_2$O/EtOH (3 mL). 0.073 mL of 2 M aqueous Na$_2$CO$_3$ solution was added, and the mixture was heated in a microwave reactor at 150° C. for 20 minutes. Methanol (2 mL) was then added. The slightly yellow solid material was collected by filtration, washed with methanol, water, methanol, and dried to give the title product. Yield: 24 mg (82%). MS (DCI/NH$_3$) m/z 546, 548 (M+H)$^+$, $^1$H NMR (400 MHz, DMSO-d$_6$): 1.16-1.40 (m, 4H), 1.61-1.67 (m, 1H), 1.73-1.79 (m, 2H), 1.95-2.01 (m, 2H), 3.37-3.41 (m, 2H), 3.57-3.64 (m, 1H), 6.80 (d, J=7.93 Hz, 1H), 7.25 (s, 1H), 7.47 (t, J=7.32 Hz, 1H), 7.55 (t, J=7.48 Hz, 2H), 7.62 (s, 1H), 8.24 (d, J=7.02 Hz, 2H), 8.61 (s, 1H), 8.92 (s, 1H).

Example 39

7-[2-chloro-6-(cyclohexylamino)pyridin-4-yl]-N-phenyl-5H-pyrrolo[2,3-b]pyrazin-2-amine A 50 mL round bottom flask charged with EXAMPLE 38A (50 mg, 0.091 mmol), aniline (11 mg, 0.110 mmol), 4,5-bis(diphenylphosphino)-9,9-dimethylxanthene (7.94 mg, 0.014 mmol), Pd(OAc)$_2$ (2 mg, 0.009 mmol) and cesium carbonate (60 mg, 0.183 mmol) was purged with nitrogen. Anhydrous dioxane (7 mL) was added, and the reaction mixture was purged with nitrogen again. The reaction mixture was heated at 80° C. for 5 hours. After cooling, the reaction mixture was partitioned between ethyl acetate and brine. The organic phase was washed with brine, and concentrated. The residue was separated by flash chromatography (eluted with 20-60% gradient EtOAc in hexane) to give 34 mg of the intermediate. This material was dissolved in dioxane (4 mL), and treated with a 50% NaOH solution in water (100 mg, 1.25 mmol) at 90° C. for 2 hours. After cooling, the reaction mixture was concentrated. The residual solid was stirred with 2 mL of water, filtered, washed with water and 1 mL of dioxane, and dried to give the title product. Yield: 16 mg. MS (DCI/NH$_3$) m/z 419 (M+H)$^+$, $^1$H NMR (400 MHz, DMSO-d$_6$): 1.13-1.31 (m, 4H), 1.54-1.58 (m, 1H), 1.67-1.72 (m, 2H), 1.88-1.93 (m, 2H), 3.57-3.62 (m, 3H), 6.54 (d, J=7.93 Hz, 1H), 6.93 (t, J=7.32 Hz, 1H), 7.02 (s, 1H), 7.32 (t, J=7.78 Hz, 2H), 7.53 (s, 1H), 7.85 (d, J=7.93 Hz, 2H), 8.00 (s, 1H), 8.21 (s, 1H), 9.36 (s, 1H), 12.18 (s, 1H).

Example 40

7-[2-chloro-6-(cyclohexylamino)pyridin-4-yl]-N-(3-phenylpropyl)-5H-pyrrolo[2,3-b]pyrazin-2-amine The title product was prepared according to the same protocol as EXAMPLE 39, substituting 3-phenylpropylamine for aniline. The crude product obtained was purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the TFA salt of the title compound. MS (DCI/NH$_3$) m/z 461 (M+H)$^+$, $^1$H NMR (400 MHz, CD$_3$OD): 1.23-1.42 (m, 6H), 1.62-1.68 (m, 1H), 1.75-1.80 (m, 2H), 1.99-2.05 (m, 4H), 2.76-2.81 (m, 2H), 3.52 (t, J=6.71 Hz, 2H), 7.08-7.26 (m, 5H), 7.43 (s, 1H), 7.57 (s, 1H), 7.68 (s, 1H), 8.02 (s, 1H).

Example 41

6-chloro-N-cyclohexyl-4-[2-(pyrazin-2-yl)-5H-pyrrolo[2,3-b]pyrazin-7-yl]pyridin-2-amine A 50 mL round bottom flask charged with EXAMPLE 38A (60 mg, 0.110 mmol), 2-(tributylstannyl)pyrazine (61 mg, 0.165 mmol), Pd$_2$(dba)$_3$ (10 mg, 0.011 mmol), and tri-o-tolylphosphine (10 mg, 0.033 mmol) was purged with nitrogen. Anhydrous DMF (7 mL) and triethylamine (0.046 mL, 0.329 mmol) were added. The reaction mixture was purged with nitrogen again, and heated at 70° C. overnight. After cooling, the reaction mixture was partitioned between ethyl acetate and brine. The organic phase was washed with brine, and concentrated. The residue was separated by flash chromatography (eluted with 10-60% gradient EtOAc in hexane) to give 25 mg of intermediate. This material was dissolved in dioxane (4 mL), and treated with 50% NaOH solution in water (80 mg) at 90° C. for 2 hours. Volatiles were removed on speedvac, and the residue was stirred with 2 mL of water for 10 minutes. The off-white solid material was collected by filtration, washed with water and dioxane, and dried to give the title product. Yield: 17 mg. MS (DCI/NH$_3$) m/z 461 (M+H)$^+$, $^1$H NMR (400 MHz, DMSO-d$_6$): 1.15-1.42 (m, 4H), 1.60-1.67 (m, 1H), 1.74-1.79 (m, 2H), 1.94-2.02 (m, 2H), 3.65-3.70 (m, 1H), 6.96 (d, J=7.93 Hz, 1H), 7.20 (s, 1H), 7.67 (s, 1H), 8.71 (s, 1H), 8.76 (dd, J=7.02, 1.83 Hz, 2H), 9.27 (s, 1H), 9.80 (s, 1H).

Example 42

7-[2-chloro-6-(cyclohexylamino)pyridin-4-yl]-N-{2-methoxy-4-[4-(4-methylpiperazin-1-yl)piperidin-1-yl]phenyl}-5H-pyrrolo[2,3-b]pyrazin-2-amine

Example 42A 1-(1-(3-methoxy-4-nitrophenyl)piperidin-4-yl)-4-methylpiperazine To a solution of 1-methyl-4-(piperidin-4-yl)piperazine (4.2 g, 22.91 mmol) in anhydrous DMF (40 mL) was added 4-fluoro-2-methoxy-1-nitrobenzene (3.92 g, 22.91 mmol) and potassium carbonate (3.80 g, 27.5 mmol). This suspension was heated at 70° C. overnight. After cooling, the reaction mixture was concentrated, and the residue partitioned between ethyl acetate and brine. The aqueous phase was extracted with ethyl acetate. The combined organic phases were concentrated. The residue was separated by flash chromatography (eluted with 0-15% of 2% ammonium hydroxide MeOH solution in dichloromethane) to give 6.88 g of the title compound. Yield: 90%. MS (DCI) m/z 335 (M+H)$^+$; $^1$H NMR (300 MHz, CDCl$_3$): δ 1.58-1.68 (m, 2H), 1.93-1.99 (m, J=11.53 Hz, 2 H), 2.29 (s, 3H), 2.44-2.51 (m, 4H), 2.62 (s, 4H), 2.92-3.02 (m, 2H), 3.90-3.98 (m, 7 H), 6.31 (d, J=2.37 Hz, 1H), 6.42 (dd, J=9.32, 2.54 Hz, 1H), 7.99 (d, J=9.49 Hz, 1H).

Example 42B 2-methoxy-4-4-(4-methylpiperazin-1-yl)piperidin-1-yl)aniline

To a solution of EXAMPLE 42A (6.88 g, 20.57 mmol) in a mixture of methanol (180 mL) and dichloromethane (20 mL) was added Raney nickel (50% in water, 3 g). This suspension was purged with hydrogen and stirred under hydrogen (40 psi) at 50° C. for 6 hours. Solid material was removed, and the filtrate was concentrated to provide the title product. Yield: 100%. MS (DCI) m/z 305 (M+H)$^+$; $^1$H NMR (300 MHz, DMSO-d$_6$): δ 1.47-1.59 (m, 2H), 1.84 (d, J=11.87 Hz, 2H), 2.33 (s, 3H), 2.44-2.71 (m, 12H), 3.28-3.48 (m, J=12.21 Hz, 4H), 3.73 (s, 2H), 6.29 (dd, J=8.31, 2.54 Hz, 1H), 6.46-6.54 (m, 2H).

Example 42C

7-[2-chloro-6-(cyclohexylamino)pyridin-4-yl]-N-{2-methoxy-4-[4-(4-methylpiperazin-1-yl)piperidin-1-yl]phenyl}-5H-pyrrolo[2,3-b]pyrazin-2-amine The title product was prepared according to the same protocol as EXAMPLE 39, substituting EXAMPLE 42B for aniline. The crude product obtained was purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the TFA salt of the title compound. MS (DCI/NH$_3$) m/z 631 (M+H)$^+$, $^1$H NMR (400 MHz, DMSO-d$_6$): 1.15-1.34 (m, 8H), 1.55-1.60 (m, 2H), 1.70-1.78 (m, 6H), 1.88-1.92 (m, 2H), 2.05-2.10 (m, 2H), 2.82 (s, 3H), 2.96-3.11 (m, 4H), 3.65-3.73 (m, 4H), 3.90 (s, 3H), 3.96 (s, 1H), 6.72-6.78 (m, 1H), 6.88-6.92 (m, 1H), 6.98 (s, 1H), 7.51 (s, 1H), 8.16-8.21 (m, 2H), 8.37 (s, 2H), 12.13 (s, 1H).

Example 43

6-chloro-N-cyclohexyl-4-{2-[(E)-2-(pyridin-4-yl)ethenyl]-5H-pyrrolo[2,3-b]pyrazin-7-yl}pyridin-2-amine A 100 mL round bottom flask charged with EXAMPLE 38A (100 mg, 0.183 mmol), Pd$_2$(dba)$_3$ (17 mg, 0.018 mmol), and tri-o-tolylphosphine (17 mg, 0.055 mmol) was purged with nitrogen. Anhydrous DMF (10 mL), 4-vinylpyridine (0.029 mL, 0.274 mmol), and triethylamine (0.076 mL, 0.549 mmol) were added. The reaction mixture was purged with nitrogen again, and heated at 80° C. overnight. After cooling, the reaction mixture was partitioned between ethyl acetate and brine. The organic phase was washed with brine, and concentrated. The residue was separated by flash chromatography (0-15% gradient of MeOH in 2:1 EtOAc in hexane) to provide 83 mg of the intermediate. This material was dissolved in dioxane (12 mL), and treated with 50% NaOH solution in water (160 mg) at 90° C. for 2 hours. Volatiles were removed, and the residue was stirred with 8 mL of water for 10 minutes. The resulting yellow solid material was collected by filtration, washed with water and dioxane, and dried to provide the title product. Yield: 44 mg. MS (DCI/NH$_3$) m/z 431 (M+H)$^+$, $^1$H NMR (400 MHz, DMSO-d$_6$): 1.18-1.40 (m, 4H), 1.58-1.62 (m, 1H), 1.74-1.77 (m, 2H), 1.96-2.01 (m, 2H), 3.28-3.32 (m, 1H), 3.65-3.70 (m, 1H), 6.89 (d, J=7.93 Hz, 1H), 7.21 (s, 1H), 7.65-7.69 (m, 3H), 7.81 (s, 2H), 8.58 (s, 1H), 8.61-8.63 (m, 3H).

Example 44

Enzyme Inhibition Data

Table 2 depicts enzyme inhibition data (K$_i$) for examples 27-43 using the same assay as example 26. In Table 2, "A" represents a K$_i$ of less than 10 nM, "B" represents a K$_i$ of between 10 nM and 100 nM, and "C" represents a K$_i$ of greater than 100 nM.

TABLE 2

| Example | Cdc7 Inhibition |
|---|---|
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | B |
| 39 | B |
| 40 | B |
| 41 | A |
| 42 | A |
| 43 | A |

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

BRIEF DESCRIPTION OF THE SEVERAL VIEWS OF THE DRAWING(S)

Not Applicable.

We claim:

1. A compound having formula (I)

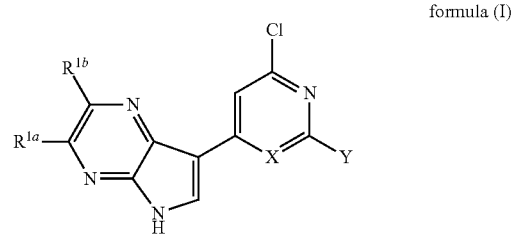

formula (I)

wherein
R$^{1a}$ and R$^{1b}$ are each hydrogen
X is N or CR$^2$;
R$^2$ is hydrogen or C$_{1-4}$-alkyl;
Y is NR$^3$R$^4$ or NR$^6$C(O)R$^7$;
R$^3$ is C$_{1-8}$-alkyl, C$_{2-8}$-alkenyl, C$_{3-8}$-cycloalkyl, heterocycloalkyl, aryl, or heteroaryl-, wherein (a) the R$^3$ C$_{1-8}$-alkyl and C$_{2-8}$-alkenyl are optionally substituted with one or more substituents selected from the group consisting of halogen, cyano, nitro, oxo, —OR$^a$, —C(O)R$^a$, —C(O)OR$^a$, —OC(O)R$^a$, —NR$^b$R$^c$, —NR$^b$C(O)R$^a$, —NHC(O)NHR$^b$, —C(O)NR$^b$R$^c$, —NHSO$_2$R$^a$, —SO$_2$NR$^b$NR$^c$, and benzyl; and (b) the R$^3$C$_{3-8}$-cycloalkyl, heterocycloalkyl, aryl, and heteroaryl are optionally substituted with one or more R$^5$;

R$^4$ is hydrogen or C$_{1-8}$-alkyl; wherein the C$_{1-8}$-alkyl is optionally substituted with one or more substituents selected from the group consisting of halogen, cyano, oxo, —OR$^a$, —C(O)R$^a$, —C(O)OR$^a$, —OC(O)R$^a$, —NR$^b$R$^c$, —NR$^b$C(O)R$^a$, —NHC(O)NHR$^b$, —C(O)NR$^b$R$^c$, —NHSO$_2$R$^a$, and —SO$_2$NR$^b$NR$^c$;

or R$^3$ and R$^4$ can be joined together to form a 4-7 membered heterocycloalkyl ring; wherein the heterocycloalkyl ring is optionally substituted with one or more R$^5$;

R$^5$ is selected from the group consisting of C$_{1-8}$-alkyl, C$_{2-8}$-alkenyl, C$_{2-8}$-alkynyl, aryl, heterocyclyl, halogen, oxo, cyano, nitro, —OR$^d$, —C(O)R$^d$, —C(O)OR$^d$, —OC(O)R$^d$, —NR$^e$R$^f$, —NR$^e$C(O)R$^d$, —NHC(O)NHR$^e$, —NHSO$_2$R$^d$, —C(O)NR$^e$R$^f$, —SR$^d$, —S(O)R$^d$, —SO$_2$R$^d$, —SO$_2$NR$^e$NR$^f$, —B(OH)$_2$, —CF$_3$, —CF$_2$CF$_3$, —OCF$_3$, and —OCF$_2$CF$_3$ wherein (a) the R$^5$C$_{1-8}$-alkyl, C$_{2-8}$-alkenyl, C$_{2-8}$-alkynyl, substituents are optionally substituted with one or more substituents selected from the group consisting of aryl, heterocyclyl, C$_{3-8}$-cycloalkyl, halogen, cyano, nitro, oxo, —OR$^d$, —C(O)R$^d$, —C(O)OR$^d$, —OC(O)R$^d$, —NR$^e$R$^f$, —NR$^e$C(O)R$^d$, —NHC(O)NHR$^e$, —C(O)NR$^e$R$^f$; and wherein (b) the R$^5$ aryl or heterocyclyl substituents are optionally substituted with one or more substituents independently selected from the group consisting of C$_{1-8}$-alkyl, C$_{2-8}$-alkenyl, C$_{2-8}$-alkynyl, aryl, heterocyclyl, halogen, cyano, nitro, oxo —OR$^g$, —C(O)R$^g$, —C(O)OR$^g$, —OC(O)R$^g$, —NR$^h$R$^i$, —NR$^h$C(O)R$^g$, —NHC(O)NHR$^h$, —NHSO$_2$R$^g$, —C(O)NR$^h$R$^i$, —SR$^g$, —S(O)R$^g$, —SO$_2$R$^g$, —SO$_2$NR$^h$NR$^i$, —CF$_3$, —CF$_2$CF$_3$, —OCF$_3$, and —OCF$_2$CF$_3$;

R$^6$ is hydrogen or C$_{1-8}$-alkyl;

R$^7$ is hydrogen, C$_{1-8}$-alkyl, C$_{2-8}$-alkenyl, C$_{2-8}$-alkynyl, C$_{3-8}$-cycloalkyl, C$_{3-8}$-cycloalkyl-(C$_{1-8}$-alkyl)-, heterocycloalkyl, heterocycloalkyl-(C$_{1-8}$-alkyl)-, aryl, aryl-(C$_{1-8}$-alkyl)-, heteroaryl-, or heteroaryl-(C$_{1-8}$-alkyl)-, wherein (a) the R$^7$C$_{1-8}$-alkyl, C$_{2-8}$-alkenyl, C$_{2-8}$-alkynyl substituents, alone or as part of another group, are optionally substituted with one or more substituents selected from the group consisting of halogen, cyano, nitro, oxo, —OR$^a$, —C(O)R$^a$, —C(O)OR$^a$, —OC(O)R$^a$, —NR$^b$R$^c$, —NR$^b$C(O)R$^a$, —NHC(O)NHR$^b$, —C(O)NR$^b$R$^c$, —NHSO$_2$R$^a$, —SO$_2$NR$^b$NR$^c$, and benzyl; and (b) the R$^7$C$_{3-8}$-cycloalkyl, heterocycloalkyl, aryl, and heteroaryl, alone or as part of another group, are optionally substituted with one or more R$^5$;

R$^a$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

R$^b$ and R$^c$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^b$ and R$^c$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

R$^d$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

R$^e$ and R$^f$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^e$ and R$^f$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

R$^g$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$; and R$^h$ and R$^i$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^h$ and R$^i$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

or a pharmaceutically acceptable salt thereof.

2. The compound of claim 1, wherein Y is NR$^3$R$^4$.

3. The compound of claim 2, wherein R$^4$ is hydrogen or methyl.

4. The compound of claim 1, wherein X is CR$^2$ and R$^2$ is hydrogen.

5. The compound of claim 1, wherein Y is NR$^6$C(O)R$^7$.

6. The compound of claim 1, wherein R$^{1a}$ and R$^{1b}$ are hydrogen, X is CR$^2$, R$^2$ is hydrogen, Y is NR$^3$R$^4$, wherein R$^3$ is C$_{1-8}$-alkyl, wherein the C$_{1-8}$-alkyl is optionally substituted with one or two substituents independently selected from the group consisting of oxo, —OR$^a$, —NR$^b$R$^c$, —NR$^b$C(O)R$^a$, and benzyl, wherein R$^4$ is hydrogen, and wherein R$^a$, R$^b$, and R$^c$ are independently selected from the group consisting of hydrogen, $C_{1-8}$-alkyl, phenyl, $C_{3-8}$-cycloalkyl, 4-7-membered heterocycloalkyl, and pyridyl.

7. The compound of claim 1, wherein $R^{1a}$ and $R^{1b}$ are hydrogen, X is $CR^2$, $R^2$ is hydrogen, Y is $NR^3R^4$, wherein $R^3$ is $C_{3-8}$-cycloalkyl, wherein the $C_{3-8}$-cycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^d$, wherein $R^4$ is hydrogen, and wherein $R^d$, $R^e$, and $R^f$ are independently selected from the group consisting hydrogen, $C_{1-8}$-alkyl, phenyl, $C_{3-8}$-cycloalkyl, 4-7-membered heterocycloalkyl, and pyridyl.

8. The compound of claim 1, wherein $R^{1a}$ and $R^{1b}$ are hydrogen, X is $CR^2$, $R^2$ is hydrogen, Y is $NR^3R^4$, wherein $R^3$ is heterocycloalkyl, wherein the heterocycloalkyl is optionally substituted with one or two substituents independently selected from the group consisting of $C_{1-8}$-alkyl, oxo, cyano, halogen, —$OR^d$, —$NR^eR^f$, —$NR^eC(O)R^d$, and —$NHSO_2R^d$, wherein $R^d$, $R^e$, and $R^f$ are independently selected from the group consisting of hydrogen, $C_{1-8}$-alkyl, phenyl, $C_{3-8}$-cycloalkyl, 4-7-membered heterocycloalkyl, and pyridyl, and wherein $R^4$ is hydrogen.

9. The compound of claim 1, wherein $R^{1a}$ and $R^{1b}$ are hydrogen, X is $CR^2$, $R^2$ is hydrogen, Y is $NR^3R^4$, wherein $R^3$ and $R^4$ are joined together to form a 4-7 membered heterocycloalkyl, wherein the heterocycloalkyl is optionally substituted with one or two substituents selected from the group consisting of $C_{1-8}$-alkyl, oxo, cyano, halogen, —$OR^d$, —$NR^eR^f$, —$NR^eC(O)R^d$, and, —$NHSO_2R^d$, wherein $R^d$, $R^e$, and $R^f$ are independently selected from the group consisting of hydrogen, $C_{1-8}$-alkyl, phenyl, $C_{3-8}$-cycloalkyl, 4-7-membered heterocycloalkyl, and pyridyl.

10. The compound of claim 1 which is
6-chloro-N-cyclohexyl-4-(5H-pyrrolo[3,2-b]pyrazin-7-yl)pyridin-2-amine;
Trans 4-(6-chloro-4-(5H-pyrrolo[3,2-b]pyrazin-7-yl)pyridin-2-ylamino)cyclohexanol;
6-chloro-N-(piperidin-3-yl)-4-(5H-pyrrolo[2,3-b]pyrazin-7-yl)pyridin-2-amine;
6-chloro-N-(1-ethylpiperidin-3-yl)-4-(5H-pyrrolo[2,3-b]pyrazin-7-yl)pyridin-2-amine;
(3-(6-chloro-4-(5H-pyrrolo[2,3-b]pyrazin-7-yl)pyridin-2-ylamino)piperidin-1-yl)(cyclopropyl)methanone;
6-chloro-N-(1-(methylsulfonyl)piperidin-3-yl)-4-(5H-pyrrolo[2,3-b]pyrazin-7-yl)pyridin-2-amine;
Trans $N^1$-(6-chloro-4-(5H-pyrrolo[2,3-b]pyrazin-7-yl)pyridin-2-yl)cyclohexane-1,4-diamine;
N-(trans-4-(6-chloro-4-(5H-pyrrolo[2,3-b]pyrazin-7-yl)pyridin-2-ylamino)cyclohexyl)cyclopropanecarboxamide;
trans-$N^1$-(6-chloro-4-(5H-pyrrolo[2,3-b]pyrazin-7-yl)pyridin-2-yl)-$N^4$,$N^4$-dimethylcyclohexane-1,4-diamine;
N-(3-(6-chloro-4-(5H-pyrrolo[2,3-b]pyrazin-7-yl)pyridin-2-ylamino)cyclohexyl)cyclopropanecarboxamide;
$N^1$-(6-chloro-4-(5H-pyrrolo[2,3-b]pyrazin-7-yl)pyridin-2-yl)-$N^3$,$N^3$-dimethylcyclohexane-1,3-diamine;
N-(3-(6-chloro-4-(5H-pyrrolo[2,3-b]pyrazin-7-yl)pyridin-2-ylamino)cyclohexyl)methanesulfonamide;
N-(6-chloro-4-(5H-pyrrolo[2,3-b]pyrazin-7-yl)pyridin-2-yl)pentanamide;
N-(6-chloro-4-(5H-pyrrolo[2,3-b]pyrazin-7-yl)pyridin-2-yl)nicotinamide;
N-(6-chloro-4-(5H-pyrrolo[2,3-b]pyrazin-7-yl)pyridin-2-yl)piperidine-4-carboxamide;
N-(6-chloro-4-(5H-pyrrolo[2,3-b]pyrazin-7-yl)pyridin-2-yl)benzamide;
$N^1$-(6-chloro-4-(5H-pyrrolo[2,3-b]pyrazin-7-yl)pyridin-2-yl)-2,2-dimethylpropane-1,3-diamine;
N-(trans 4-(6-chloro-4-(5H-pyrrolo[3,2-b]pyrazin-7-yl)pyridin-2-ylamino)cyclohexyl)-5-oxopyrrolidine-2-carboxamide;
4-chloro-N-cyclohexyl-6-(5H-pyrrolo[3,2-b]pyrazin-7-yl)pyrimidin-2-amine;
N-(trans 4-((6-chloro-4-(5H-pyrrolo[2,3-b]pyrazin-7-yl)pyridin-2-yl)(ethyl)amino)cyclohexyl)cyclopropanecarboxamide;
N-(3-(6-chloro-4-(5H-pyrrolo[2,3-b]pyrazin-7-yl)pyridin-2-ylamino)cyclohexyl)-2-(dimethylamino)acetamide;
N-(3-((6-chloro-4-(5H-pyrrolo[2,3-b]pyrazin-7-yl)pyridin-2-yl)(ethyl)amino)cyclohexyl)-2-(dimethylamino)acetamide; or
N-(3-(6-chloro-4-(5H-pyrrolo[2,3-b]pyrazin-7-yl)pyridin-2-ylamino)cyclohexyl)furan-2-sulfonamide.

11. A pharmaceutical composition comprising a compound of claim 1, or pharmaceutically acceptable salt thereof, and a pharmaceutically acceptable excipient.

* * * * *